US011631798B2

(12) United States Patent
Choi et al.

(10) Patent No.: US 11,631,798 B2
(45) Date of Patent: Apr. 18, 2023

(54) BONDING INTERPOSER AND INTEGRATED CIRCUIT CHIP, AND ULTRASOUND PROBE USING THE SAME

(71) Applicants: SAMSUNG ELECTRONICS CO., LTD., Suwon-si (KR); Dong Won Shin, Incheon (KR)

(72) Inventors: Kyung-moo Choi, Yongin-si (KR); Dong Won Shin, Incheon (KR)

(73) Assignees: SAMSUNG ELECTRONICS CO., LTD., Suwon-si (KR); Dong Won Shin, Incheon (KR)

( * ) Notice: Subject to any disclaimer, the term of this patent is extended or adjusted under 35 U.S.C. 154(b) by 1158 days.

(21) Appl. No.: 16/038,348

(22) Filed: Jul. 18, 2018

(65) Prior Publication Data

US 2019/0027675 A1     Jan. 24, 2019

(30) Foreign Application Priority Data

Jul. 18, 2017   (KR) ........................ 10-2017-0091052

(51) Int. Cl.
*H01L 41/047*  (2006.01)
*G01S 7/52*    (2006.01)
(Continued)

(52) U.S. Cl.
CPC ........ *H01L 41/0475* (2013.01); *A61B 8/4461* (2013.01); *B06B 1/0622* (2013.01);
(Continued)

(58) Field of Classification Search
CPC ............. A61B 8/4461; G01N 29/2437; H01L 41/0475; H01L 41/09; H01L 41/11;
(Continued)

(56) References Cited

U.S. PATENT DOCUMENTS 4,803,595 A * 2/1989 Kraus ................ H01L 23/5385
174/262
5,386,627 A * 2/1995 Booth ................ H01L 23/5382
29/830
(Continued)

FOREIGN PATENT DOCUMENTS

CN        1336450 A       2/2002
CN      103985807 A       8/2014
(Continued)

OTHER PUBLICATIONS

Communication dated May 10, 2021 issued by the European Patent Office in application No. 18184278.2.
(Continued)

*Primary Examiner* — Jeffrey T Carley
(74) *Attorney, Agent, or Firm* — Sughrue Mion, PLLC

(57) ABSTRACT

The method of bonding an interposer and an integrated circuit chip includes preparing an interposer including an insulator and conductive lines each having one end exposed to a first surface of the insulator and another end exposed to a second surface opposite to the first surface; placing a bonding mask on the interposer; forming through-holes on the bonding mask before or after the placing of the bonding mask on the interposer; filling the plurality with a conductive material; and bonding an integrated circuit chip to the bonding mask.

4 Claims, 30 Drawing Sheets

(51) Int. Cl.
- *G01S 15/89* (2006.01)
- *A61B 8/00* (2006.01)
- *B06B 1/06* (2006.01)
- *G01N 29/24* (2006.01)
- *H01L 21/48* (2006.01)
- *H01L 23/538* (2006.01)
- *H01L 23/00* (2006.01)
- *H01L 25/16* (2023.01)
- *H01L 41/09* (2006.01)
- *H01L 41/25* (2013.01)

(52) U.S. Cl.
CPC ...... *G01N 29/2437* (2013.01); *G01S 7/52079* (2013.01); *G01S 15/892* (2013.01); *G01S 15/8925* (2013.01); *H01L 21/486* (2013.01); *H01L 23/5386* (2013.01); *H01L 24/11* (2013.01); *H01L 24/81* (2013.01); *H01L 25/16* (2013.01); *H01L 41/09* (2013.01); *H01L 41/25* (2013.01); *A61B 2562/12* (2013.01); *G01S 7/5208* (2013.01); *H01L 24/13* (2013.01); *H01L 24/16* (2013.01); *H01L 2224/11334* (2013.01); *H01L 2224/16112* (2013.01); *H01L 2224/16235* (2013.01); *H01L 2224/16237* (2013.01); *H01L 2224/816* (2013.01); *H01L 2224/81007* (2013.01); *H01L 2224/8114* (2013.01); *H01L 2224/8159* (2013.01); *H01L 2224/81191* (2013.01); *H01L 2224/81385* (2013.01); *H01L 2224/81855* (2013.01); *H01L 2924/1433* (2013.01)

(58) Field of Classification Search
CPC ......... H01L 41/25; H01L 24/11; H01L 24/16; B06B 1/0622
See application file for complete search history.

(56) References Cited

U.S. PATENT DOCUMENTS

| | | | | |
|---|---|---|---|---|
| 5,854,534 A * | 12/1998 | Beilin | ............... | H05K 1/144 |
| | | | | 257/E23.067 |
| 6,586,112 B1 | 7/2003 | Te | | |
| 8,273,603 B2 * | 9/2012 | Racz | ............... | H01L 23/13 |
| | | | | 257/787 |
| 8,659,212 B2 | 2/2014 | Eggen et al. | | |
| 9,408,589 B2 * | 8/2016 | Ko | ............... | A61B 8/5207 |
| 10,137,477 B2 * | 11/2018 | Petersen | ............... | B06B 1/0207 |
| 10,164,602 B2 | 12/2018 | Park et al. | | |
| 10,658,563 B2 * | 5/2020 | Kim | ............... | B06B 1/0685 |
| 10,898,925 B2 | 1/2021 | Dekker et al. | | |
| 2003/0164548 A1 * | 9/2003 | Lee | ............... | H01L 24/81 |
| | | | | 257/E21.511 |
| 2007/0285884 A1 * | 12/2007 | Lee | ............... | H01L 23/4985 |
| | | | | 257/E23.07 |
| 2008/0157361 A1 * | 7/2008 | Wood | ............... | H01L 23/3114 |
| | | | | 257/E21.597 |
| 2008/0265399 A1 * | 10/2008 | Chao | ............... | H01L 23/49827 |
| | | | | 257/698 |
| 2010/0081236 A1 * | 4/2010 | Yang | ............... | H01L 24/94 |
| | | | | 257/E21.511 |
| 2010/0109142 A1 * | 5/2010 | Toh | ............... | H01L 23/3135 |
| | | | | 257/E23.06 |
| 2011/0031598 A1 * | 2/2011 | Lee | ............... | H01L 25/0657 |
| | | | | 257/E21.705 |
| 2011/0248603 A1 * | 10/2011 | Tezuka | ............... | G01K 11/04 |
| | | | | 29/25.35 |
| 2013/0092935 A1 * | 4/2013 | Wang | ............... | H01L 23/49827 |
| | | | | 257/E23.002 |
| 2015/0055312 A1 * | 2/2015 | Lee | ............... | H05K 3/4661 |
| | | | | 174/262 |
| 2016/0207068 A1 | 7/2016 | Dekker et al. | | |

FOREIGN PATENT DOCUMENTS

| | | | | |
|---|---|---|---|---|
| CN | 105492128 A | 4/2016 | | |
| CN | 106129047 A | 11/2016 | | |
| CN | 106312206 A | 1/2017 | | |
| CN | 106413921 A | 2/2017 | | |
| CN | 106533384 A | 3/2017 | | |
| CN | 106572610 A | 4/2017 | | |
| JP | 2013235884 A | 11/2013 | | |
| KR | 10-2005-0071857 A | 7/2005 | | |
| KR | 10-2013-0094751 A | 8/2013 | | |
| WO | 03/000337 A2 | 1/2003 | | |
| WO | 2006/075283 A2 | 7/2006 | | |
| WO | WO-2013118768 A1 * | 8/2013 | ........... | A61B 5/0095 |
| WO | 2015/077593 A1 | 5/2015 | | |

OTHER PUBLICATIONS

Communication dated Jul. 6, 2021 issued by the State Intellectual Property Office of the P.R. China in application No. 201810782185.4.
Communication dated Nov. 30, 2018, issued by the European Patent Office in counterpart European Application No. 18184278.2.
Communication dated Nov. 25, 2020 issued by the State Intellectual Property Office of P.R. China in English counterpart Chinese Application No. 201810782185.4.
Communication dated Jan. 7, 2022, issued by the Korean Intellectual Property Office in Korean Patent Application No. 10-2017-0091052.
Communication dated Jul. 19, 2022, issued by the Korean Intellectual Property Office in application No. 10-2017-0091052.
Communication dated Oct. 31, 2022, issued by the European Patent Office in counterpart European Application No. 18184278.2.

* cited by examiner

BONDING INTERPOSER AND INTEGRATED CIRCUIT CHIP, AND ULTRASOUND PROBE USING THE SAME

CROSS-REFERENCE TO RELATED APPLICATION(S)

This application is based on and claims priority under 35 U.S.C. § 119 to Korean Patent Application No. 10-2017-0091052, filed on Jul. 18, 2017, in the Korean Intellectual Property Office, the disclosure of which is incorporated by reference herein in its entirety.

BACKGROUND

1. Field

The disclosure relates to an ultrasound probe and a method of manufacturing the ultrasound probe, and more particularly, to bonding an interposer and an integrated circuit chip and an ultrasound probe using the same.

2. Description of Related Art

An ultrasound diagnostic apparatus emits ultrasound signals generated by a transducer of an ultrasound probe to an object, receives information of signals reflected by the object, and obtains an image, for example, an image of soft tissue or blood flow of the object.

An ultrasound probe may be a one-dimensional (1D) probe capable of imaging a line region and a two-dimensional (2D) probe capable of imaging a surface region. The 1D probe has transducer elements which are configured to transmit and receive ultrasound signals and arranged in a single line and the 2D probe has transducer elements which are arranged in a matrix structure. However, it might be difficult to provide reliable electrical and signal interconnections for the transducer elements of the 2D probe that are arranged distally to the periphery of the matrix structure.

SUMMARY

Additional aspects will be set forth in part in the description which follows and, in part, will be apparent from the description, or may be learned by practice of the presented embodiments.

In accordance with an aspect of the disclosure, a method of bonding an interposer and an integrated circuit chip includes preparing an interposer including an insulator and a plurality of conductive lines each having one end exposed to a first surface of the insulator and another end exposed to a second surface, which is opposite to the first surface; placing a bonding mask on the interposer; forming a plurality of through-holes on the bonding mask before or after the placing of the bonding mask on the interposer; filling the plurality of through-holes with a conductive material; and bonding an integrated circuit chip to the bonding mask.

The bonding of the integrated circuit chip to the bonding mask may be achieved by a flip-chip-bonding technique.

Bump balls may be placed on electrode terminals of the integrated circuit chip, and the bump balls may be inserted into the plurality of through-holes when the integrated circuit chip is aligned with the bonding mask.

The conductive material may be conductive epoxy.

The forming of the plurality of through-holes on the bonding mask after the placing of the bonding mask on the interposer may be achieved by laser emission.

The bonding mask may be a transparent film.

In accordance with an aspect of the disclosure, an ultrasound probe includes a 2D acoustic module including piezoelectric elements arranged in two dimensions; an interposer placed on a rear surface of the 2D acoustic module and including an insulator and a plurality of conductive lines each having one end exposed to a first surface of the insulator and another end exposed to a second surface, which is opposite to the first surface; an integrated circuit chip; and a bonding mask placed between the integrated circuit chip and the interposer and including a plurality of through-holes and a conductive material with which the plurality of through-holes are filled.

BRIEF DESCRIPTION OF THE DRAWINGS

The above and other aspects, features, and advantages of certain embodiments of the present disclosure will be more apparent from the following description taken in conjunction with the accompanying drawings, in which.

DETAILED DESCRIPTION

Figure 1:
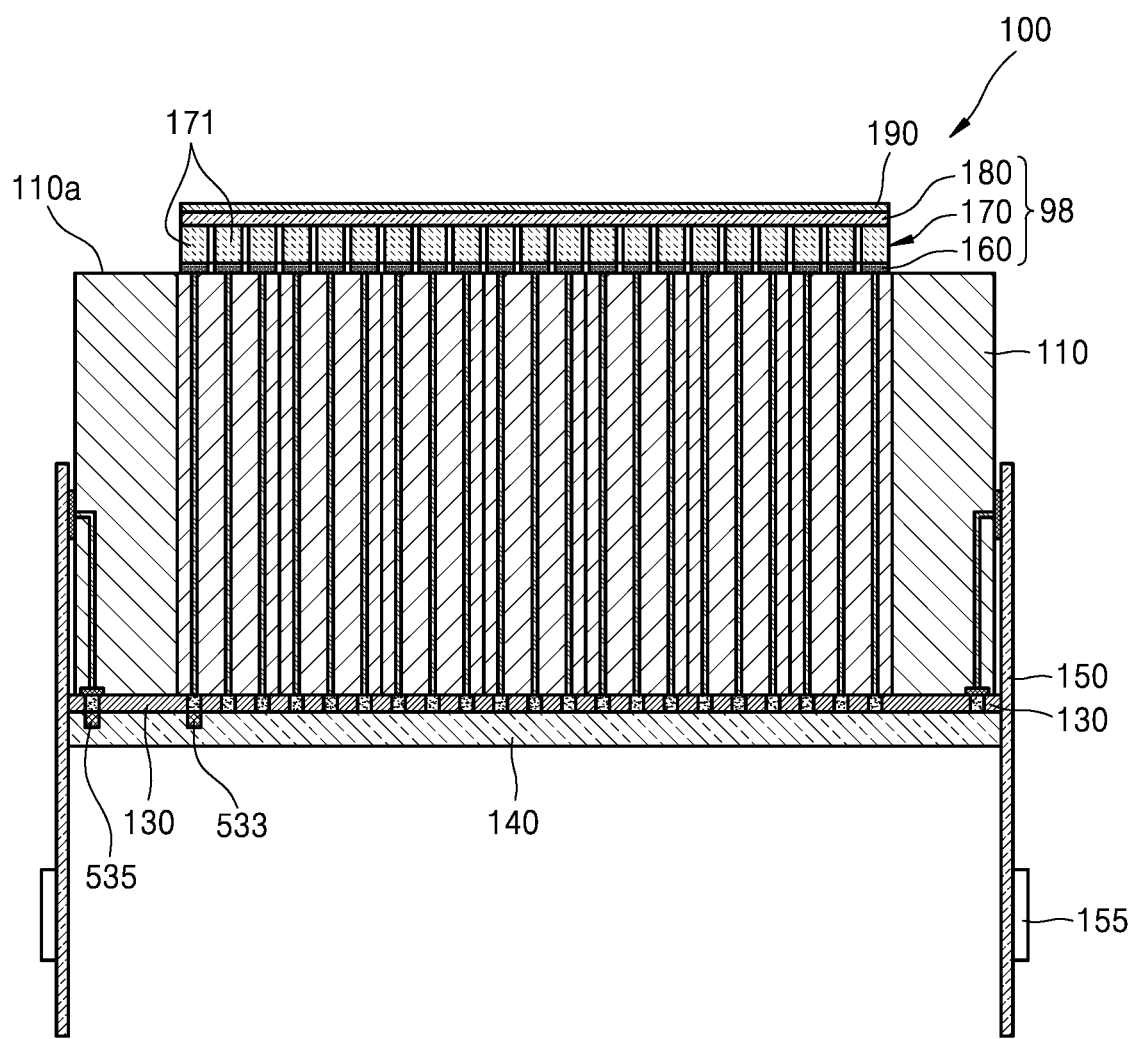
FIG. 1 shows a schematic cross-section of an ultrasound probe according to an embodiment.

Reference will now be made in detail to embodiments, examples of which are illustrated in the accompanying drawings, wherein like reference numerals refer to like elements throughout. In this regard, the embodiments may have different forms and should not be construed as being limited to the descriptions set forth herein. Accordingly, the embodiments are merely described below, by referring to the figures, to explain aspects.

The present disclosure does not describe all elements of embodiments, and a general description in a technical field to which the present disclosure belongs or a repetitive description in the embodiments will be omitted. As used herein, the term "module" or "unit" may be embodied in one or more combinations of software, hardware, and firmware. Depending on embodiments, a plurality of "modules" or "units" may be implemented as a single element, or a single "module" or "unit" may include a plurality of elements.

The term "object" as used herein refers to be a target to be photographed and may include person, animal, or part thereof. For example, the object may include a human part (e.g., an organ), a phantom, or the like.

Through the specification, the term "ultrasound image" refers to an image of an object that is processed on the basis of ultrasound signals transmitted to and reflected by the object.

FIG. 1 shows a schematic cross-section of an ultrasound probe 100 according to an embodiment.

Referring to FIG. 1, the ultrasound probe 100 includes a piezoelectric layer 170 composed of a plurality of piezoelectric elements 171. The piezoelectric layer 170 is used as an ultrasound transducer for delivering acoustic energy to an object 610 (refer to FIG. 11), receiving ultrasound echoes returned from the object 610, and converting the received echoes into electric signals to perform processing and displaying. The piezoelectric elements 171 of the piezoelectric layer 170 may be arranged in two dimensions. Here, the 2D arrangement may refer to, for example, an arrangement of two or more columns and two or more rows, but is not limited thereto. All the piezoelectric elements 171 may be arranged on a single surface or arranged in a curved shape to be used for a convex or concave arrangement. The piezoelectric elements 171 of the piezoelectric layer 170 may be made of piezoelectric materials such as ceramics or polymers and formed in a rod shape or a convex shape. The piezoelectric layer 170 may be cut or diced into rows and columns to form an arrangement of the piezoelectric elements 171. The piezoelectric elements 171 may be separated into hundreds to tens of thousands of piezoelectric elements and thus arranged in tens to hundreds of rows and tens to hundreds of columns. The piezoelectric elements 171 may be equally spaced from one another, but are not limited thereto. The space between the piezoelectric elements 171 is known as a kerf. The kerf may be filled with any filling material, that is, an air or an attenuation material with low acoustic impedance in order to prevent transfer of, or absorb, vibration between adjacent piezoelectric elements 171.

A lower electrode layer 160 is provided under the piezoelectric layer 170. The lower electrode layer 160 may be formed of a material with high conductivity and high acoustic impedance. For example, the lower electrode layer 160 may be formed of a material such as tungsten or a tungsten carbide. The lower electrode layer 160 has a plurality of lower electrodes separated apart from one another to correspond to, and prevent electrical interconnection between, the piezoelectric elements 171 of the piezoelectric layer 170.

An acoustic matching layer 180 is provided on the piezoelectric layer 170.

A common electrode layer may be provided between the piezoelectric layer 170 and the acoustic matching layer 180. When the acoustic matching layer 180 is formed of a conductive material, the acoustic matching layer 180 itself may function as a common electrode layer.

An acoustic lens layer 190 may be provided on the acoustic matching layer 180. The acoustic lens layer 190 may be omitted.

The piezoelectric layer 170, the acoustic matching layer 180, and the acoustic lens layer 190, which have been described above, constitute a 2D acoustic module 98.

An electrical interconnection assembly for electrical wiring of each of the piezoelectric elements 171 of the piezoelectric layer 170 is provided under the 2D acoustic module.

The electrical interconnection assembly includes an integrated circuit chip 140 that is electrically connected to the 2D acoustic module via the interposer 110 and a bonding mask 130. As described above, the piezoelectric layer 170 may have thousands of piezoelectric elements 171 in which signals are transmitted or received independently. Since a cable for electrically connecting the ultrasound probe to a main body of an ultrasound diagnostic apparatus has a limitation on the number of wirings, it is not easy to include all wirings corresponding to the piezoelectric elements 171 on a one-to-one basis in the cable. The integrated circuit chip 140 may be an application specific integrated circuit (ASIC) including a circuit for reducing the number of wires needed for communication between the ultrasound diagnostic apparatus and any external source in the ultrasound diagnostic apparatus. The integrated circuit chip 140 may have a surface-mounted package, such as a ball grid array (BGA), where electrode terminals are arranged on a flat plate surface. The integrated circuit chip 140 includes first terminals 533 provided on the flat plate surface. Here, first terminals correspond to the piezoelectric elements 171 of the piezoelectric layer 170 on a one-to-one basis, and Tx/Rx signals are transferred to the first terminals. The integrated circuit chip 140 includes second terminals 535 for transmitting and receiving electrical signals to and from an external source to supply power to, and control, the integrated circuit chip 140. Second terminals may also be formed on the flat plate surface on which the first terminals are formed and on outer sides of the first terminals.

An interposer 110 is provided between the 2D acoustic module and the integrated circuit chip 140. The interposer 110 will be described in detail when a manufacturing method is described later.

One or more electrode pads 1155 (refer to FIG. 2G) for electrical interconnection of the second terminals of the integrated circuit chip 140 may be additionally included on a side surface of the interposer 110.

A flexible printed circuit board 150 for external wirings may be attached to the side surface of the interposer 110. For example, an electrode pad 155 of the flexible printed circuit board 150 may be brought into contact with conductive wires of an outwardly extending cable. The conductive wires of the cable may be connected to the electrode pad 1155 located on the side surface of the interposer 110, without the flexible printed circuit board 150.

FIGS. 2A to 2H illustrate a method of manufacturing an interposer according to an embodiment.

Figure 2A:
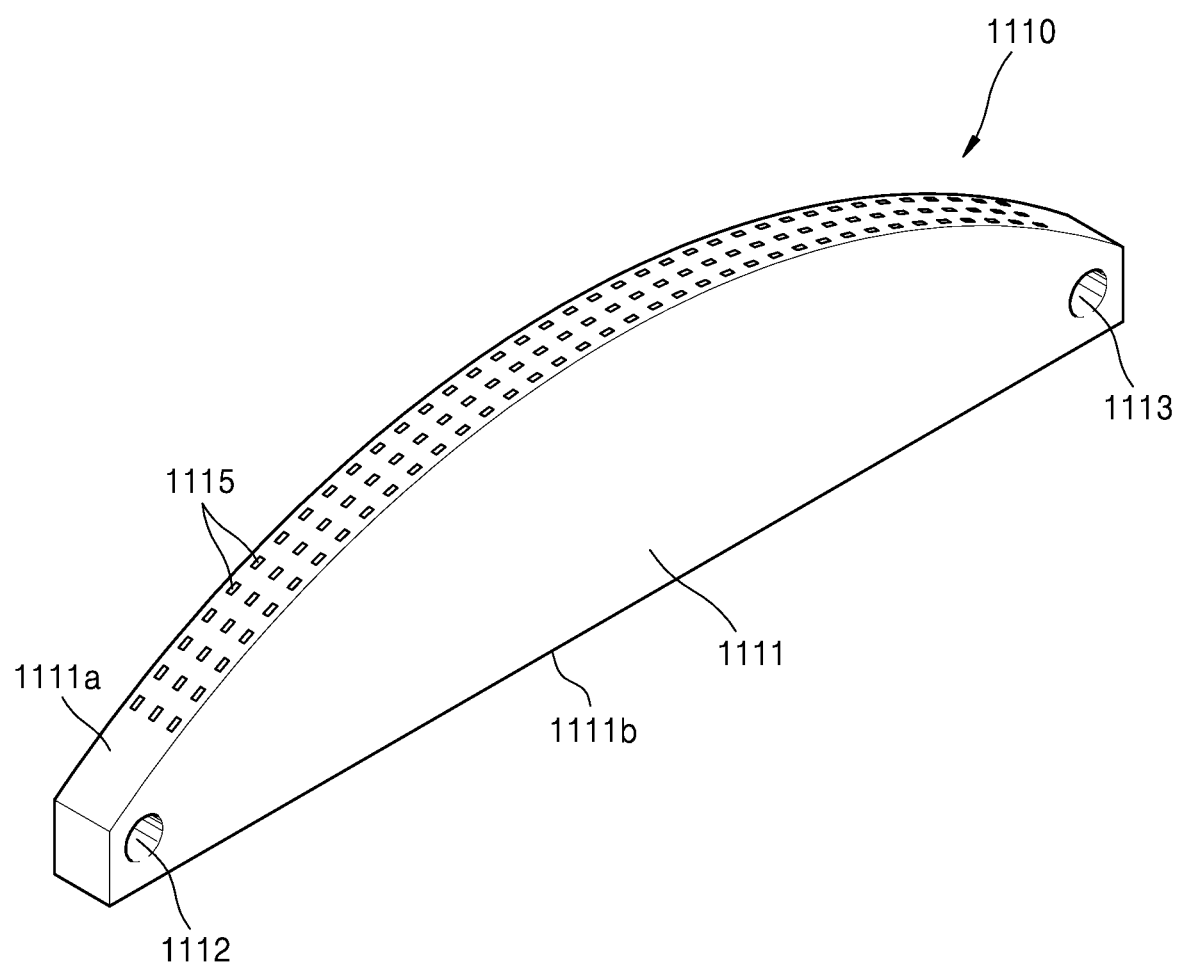
FIGS. 2A, 2B, 2C, 2D, 2E, 2F, 2G, and 2H illustrate a method of manufacturing an interposer according to an embodiment.

Referring to FIG. 2A, one or more circuit boards 1110 are prepared. The circuit board 1110 includes an insulator 1111 with a flat plate shape. As can be seen in a partial sectional view of FIG. 2B, first conductive lines 1115 are provided inside the insulator 1111 and arranged in at least one column. The arrangement of the first conductive lines 1115 corresponds to that of the piezoelectric elements 171 of the piezoelectric layer 170. That is, the number of first conductive lines 1115 in one column of the arrangement of the first conductive lines 1115 is equal to the number of piezoelectric elements 171 in one column of the arrangement of the piezoelectric elements 171. The pitch of the first conductive lines 1115 corresponds to the pitch of the piezoelectric elements 171 of the piezoelectric layer 170. A first side portion 1111a, i.e., an upper surface, of the insulator 1111 may have a curved shape, and a second side portion 1111b, i.e., a lower surface, which is opposite to the first side portion 1111a, may have a flat plate shape. Ends of each of the first conductive lines 1115 are exposed to the first side portion 1111a and the second side portion 1111b of the insulator 1111. First ends 1122 of the first conductive lines 1115 exposed to the first side portion 1111a are electrically connected to the lower electrodes of the lower electrode layer 160 on a one-to-one basis. Second ends 1124 of the first conductive lines 1115 exposed to the second side portion 1111b are electrically connected to the first terminals of the integrated circuit chip 140, a bonding mask 130 being interposed between the second ends and the first terminals.

Figure 2B:
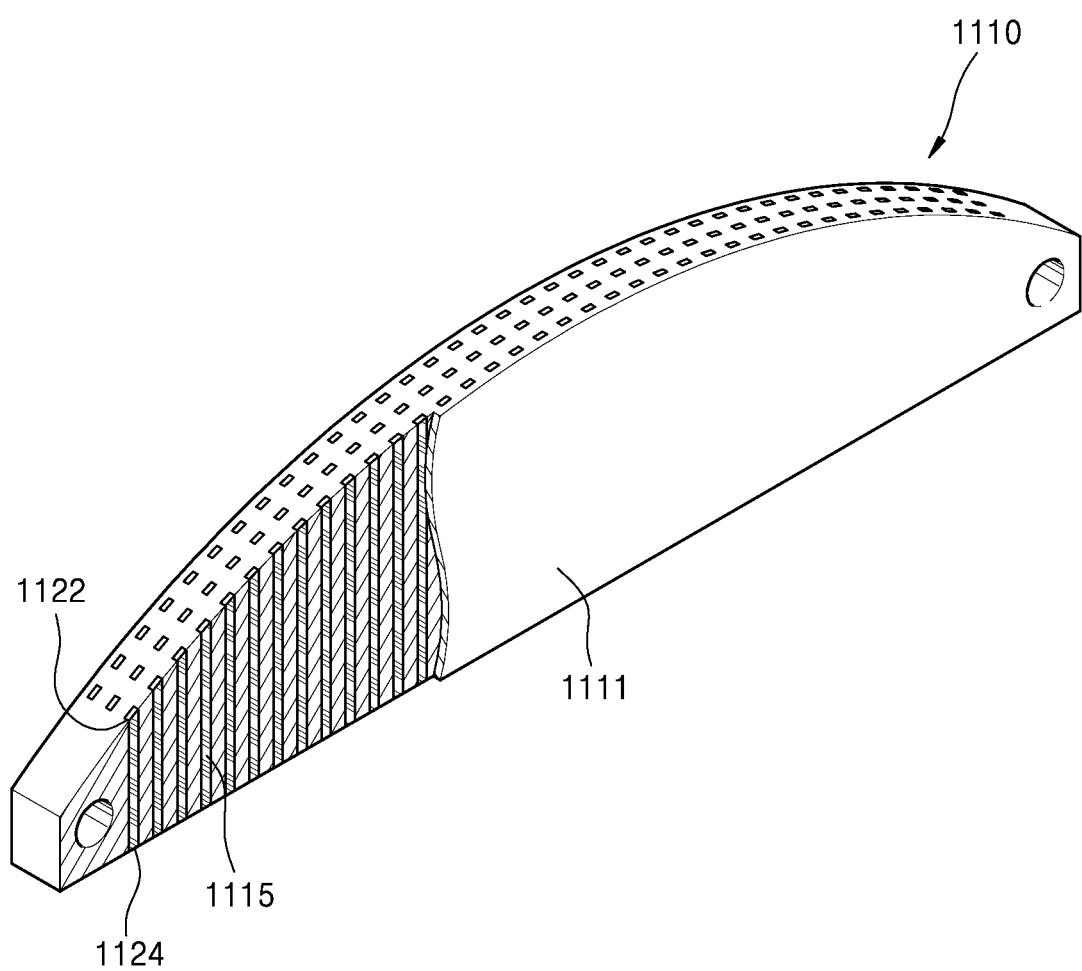

FIGS. 2A and 2B show that three columns of first conductive lines 1115 are arranged in one circuit board 1110, but the present disclosure is not limited thereto.

Because the piezoelectric layer 170 is located on the first side portion 1111a of the insulator 1111, the curved shape of the first side portion 1111a defines a curved shape of the piezoelectric layer 170 and also defines a curved surface of the ultrasound probe 100 that is in contact with an object 610 (refer to FIG. 12).

Guide holes 1112 and 1113, which serve as a first guide portion when a plurality of circuit boards being stacked, may be provided on the circuit board 1110. The number or positions of the guide holes 1112 and 1113 may be set such that the first conductive lines 1115 are not obstructed and do not limit embodiments of the present disclosure. The guide holes 1112 and 1113, which are examples of a means for performing guidance when the circuit boards 1110 are stacked, may be modified in various shapes. For example, a groove, instead of a hole, may be formed at one side portion of the circuit board 1110 such that such a groove serves as a guide when the circuit boards 1110 are stacked.

Figure 2C:
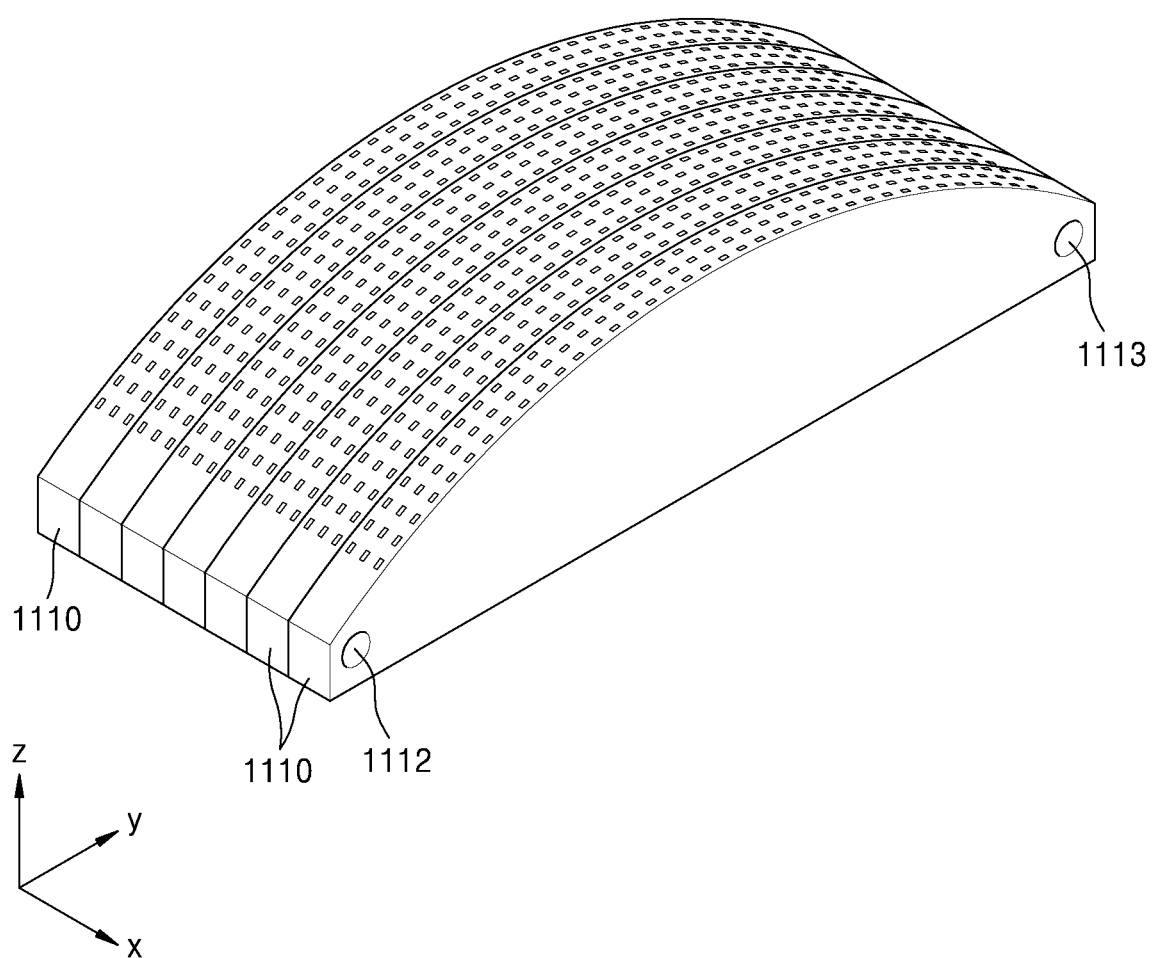

Referring to FIG. 2C, the circuit boards 1110 are stacked such that the first side portions 1111a are coplanar with each other, e.g., located at a same plane, and the second side portions 1111b are coplanar with each other, e.g., located at a same plane. It is possible to facilitate the arrangement of the circuit boards 1110 during the stacking process by using the guide holes 1112 and 1113 when the circuit boards are stacked.

Figure 2D:
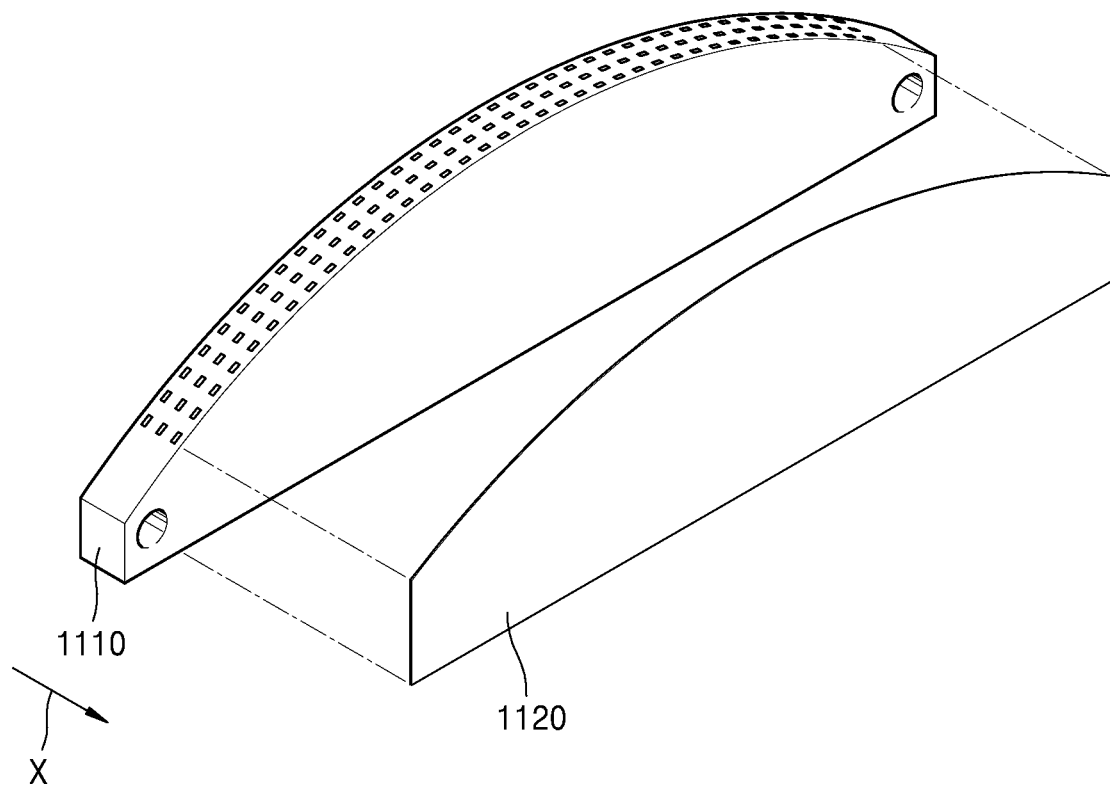
Figure 2E:
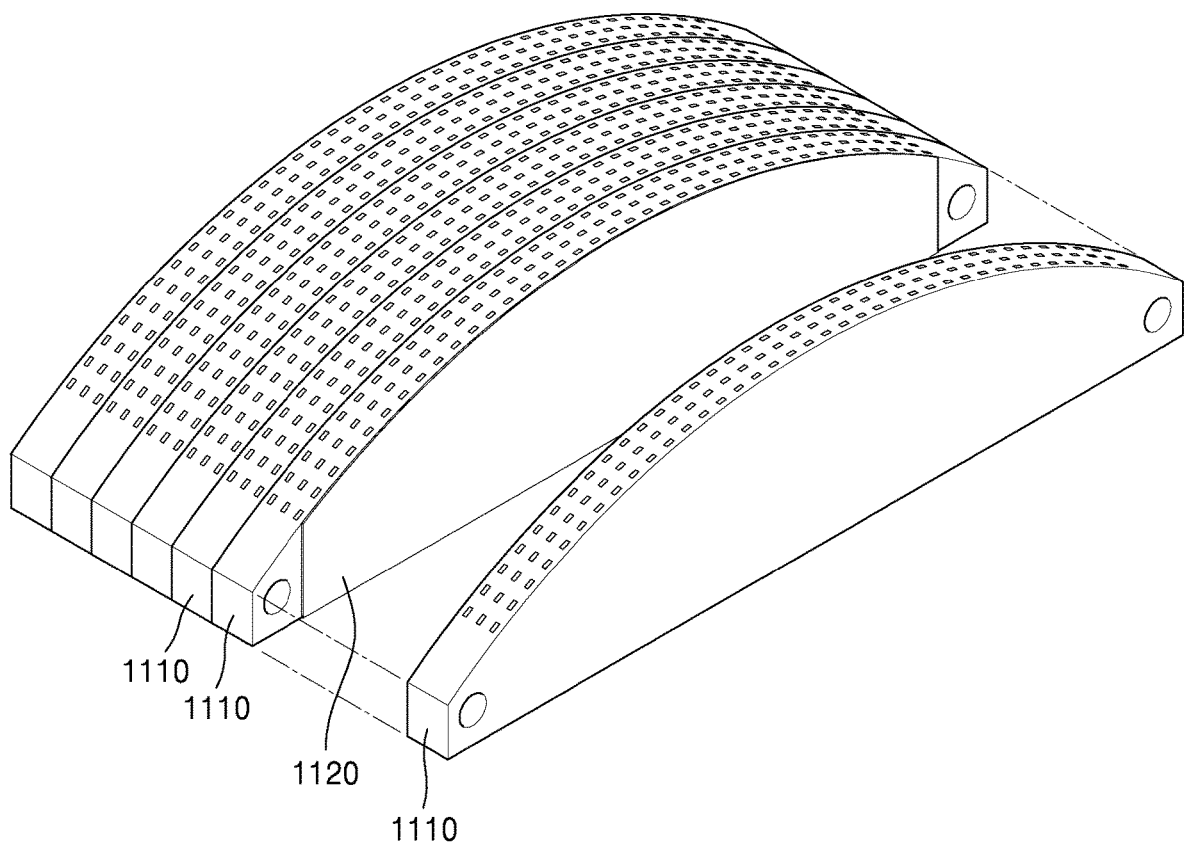

Referring to FIGS. 2D and 2E, when the circuit boards 1110 are stacked, e.g., into a board stack, the pitch of the first conductive lines 1115 in a stacking direction x allow a film 1120 to be interposed between the circuit boards 1110. By inserting the film 1120 into a stack structure of the circuit boards 1110, it is possible to ensure a pitch required by the circuit boards 1110 and the first conductive lines 1115, for example, included in the adjacent circuit boards 1110.

Figure 2F:
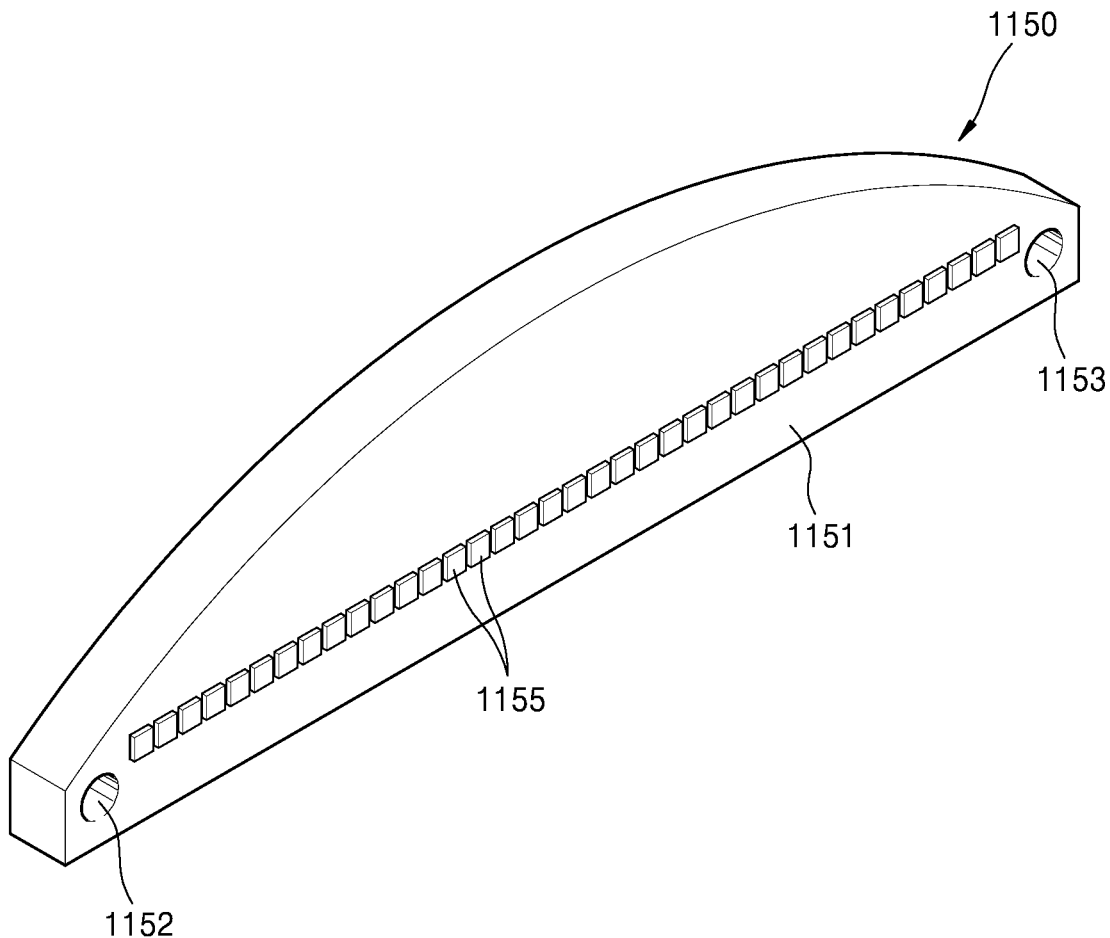
Figure 2G:
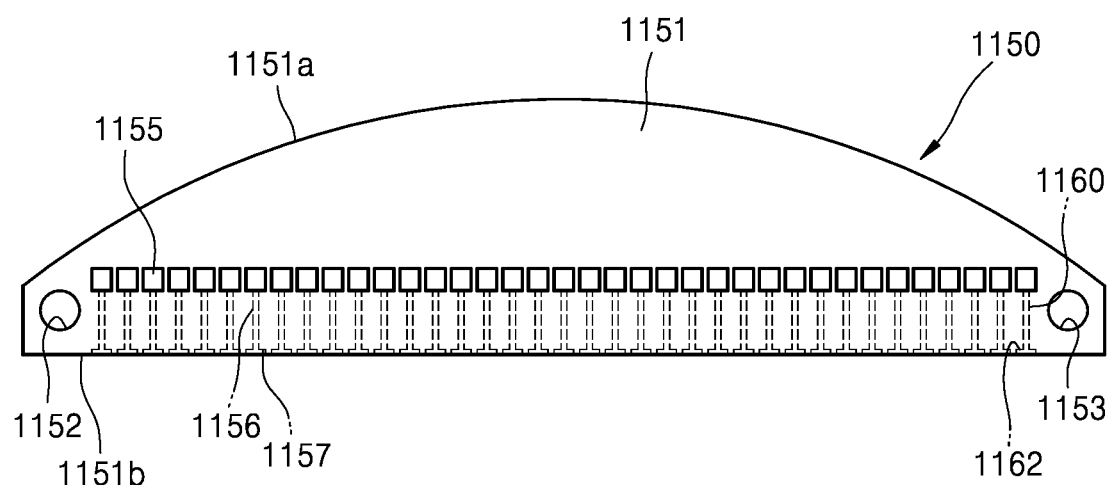

Referring to FIGS. 2F and 2G, one or more outer substrates 1150 are prepared. FIG. 2F is a perspective view of the outer substrate 1150, and FIG. 2G is a side view of the outer substrate 1150. As shown in FIGS. 2F and 2G, the outer substrate 1150 has the same external shape as the circuit board 1110. That is, a first side portion 1151a, i.e., an upper surface, of the outer substrate 1150 has the same curved surface as that of the first side portion 1111a of the circuit board 1110, and a second side portion 1151b, i.e., a lower surface, of the outer substrate 1150 has the same flat surface as that of the second side portion 1111b of the circuit board 1110. The outer substrate 1150 may have guide holes 1152 and 1153, i.e., a second guide portion.

Second conductive lines 1156 are located inside the outer substrate 1150. First ends 1160 of the second conductive lines 1156 are exposed to an outer flat plate surface of the outer substrate 1150, and the second ends 1162 of the second conductive lines 1156 are exposed to the second side portion 1151b. FIG. 2F and FIG. 2G show a case in which the second conductive lines 1156 are arranged in one column, but the present disclosure is not limited thereto. The second conductive lines 1156 may be arranged in a plurality of columns. At the first ends of the second conductive lines 1156 exposed to the outer flat plate surface of the outer substrate 1150, electrode pads 1155 may be formed on an outer side surface 1151 of the outer substrate 1150 to facilitate electrical interconnection. FIG. 2F and FIG. 2G show a case in which the electrode pads 1155 are arranged in one column, but the present disclosure is not limited thereto. The electrode pads 1155 may be arranged in a plurality of columns. At the second ends of the second conductive lines 1156 exposed to the second side portion 1151b, pads 1157 may be formed to facilitate electrical interconnection. The pads 1157 may be formed adjacent an inner surface of the second side portion 1151b or outside second side portion 1151b.

The second side portion 1151b of the outer substrate 1150 is in contact with the integrated circuit chip 140 via the bonding mask 130 being interposed therebetween. Thus, the second ends of the second conductive lines 1156 are electrically connected to the second terminals of the integrated circuit chip 140.

Figure 2H:
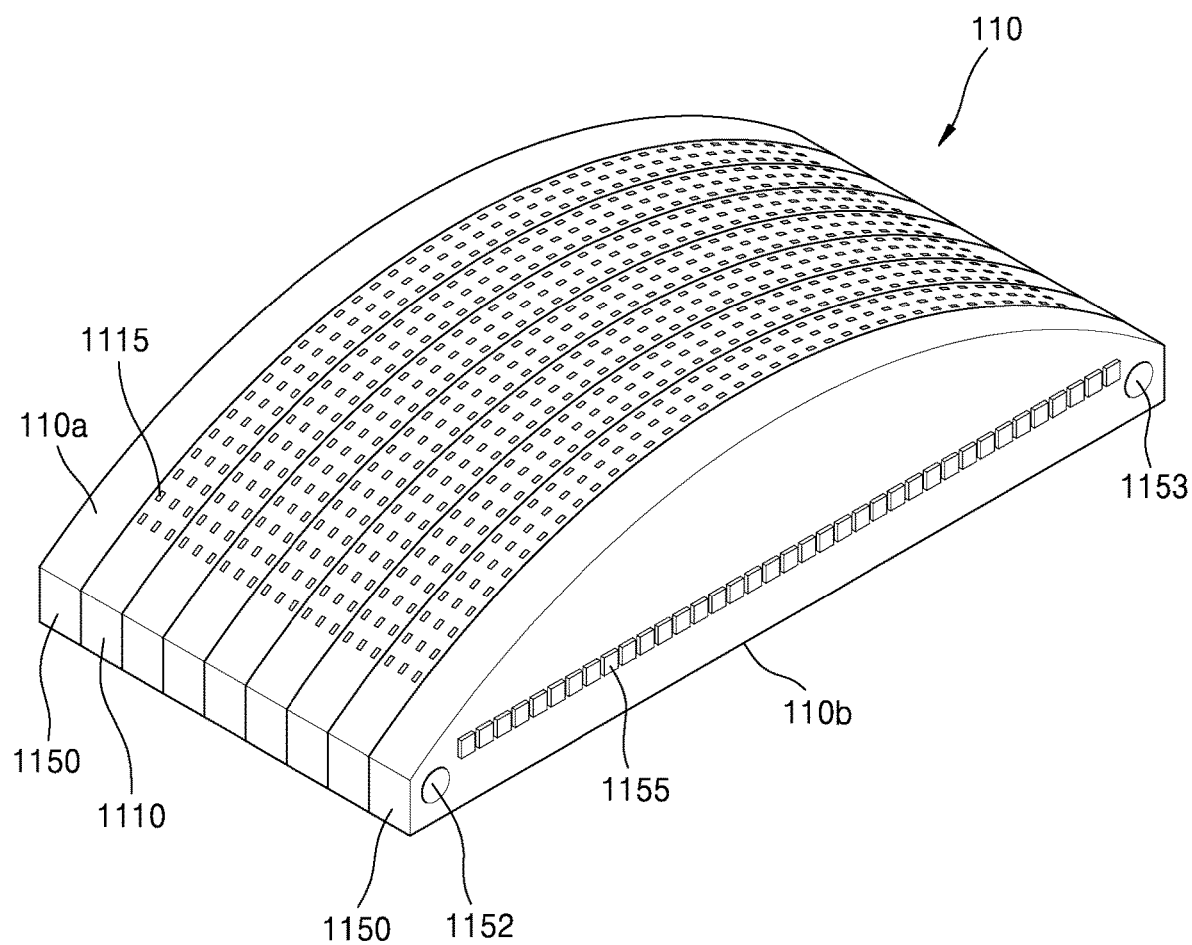

FIG. 2H shows a complete configuration of the interposer 110, i.e., a board stack, in which outer substrates 1150 are placed at both outer sides of a stack structure of the circuit boards 1110. The outer substrates 1150 may have a horizontally symmetrical structure, but are not limited thereto. Also, in some cases, either of the outer substrates may be omitted.

In an embodiment, the interposer 110 has an upper surface 110a to which the first ends of the first conductive lines 1115 are exposed and a lower surface 110b to which the second ends of the first and second conductive lines 1115 and 1156 are exposed. In this case, the first ends of the first conductive lines 1115 are to be electrically connected to the piezoelectric elements 171, and the second ends of the first conductive lines 1115 are to be electrically connected to the first terminals of the integrated circuit chip 140. The second ends of the second conductive lines 1156 located at the outer side are to be electrically connected to the second terminals of the integrated circuit chip 140. The first ends of the second conductive lines 1156 are exposed to a side surface of the interposer 110 to form electrode pads 1155 so as to enable electrical interconnection to the outside.

FIGS. 3A to 3G illustrate a method of manufacturing an electrical interconnection assembly according to an embodiment.

Figure 3A:
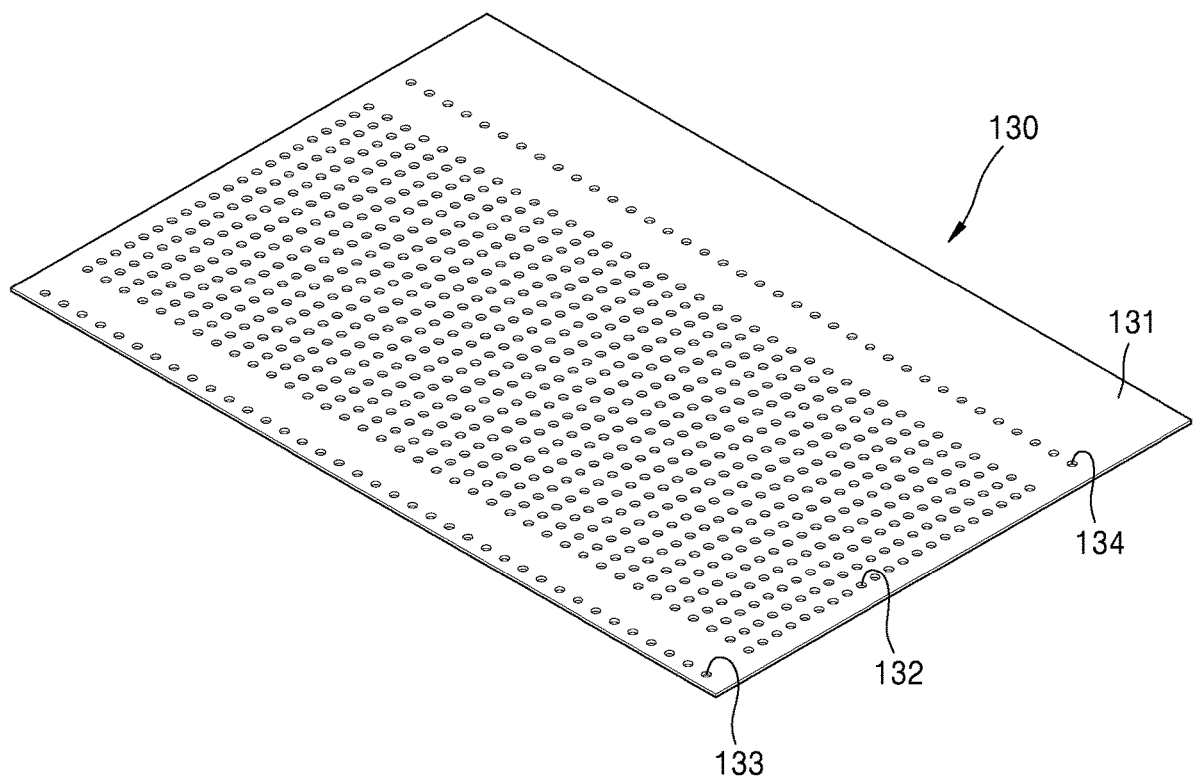
FIGS. 3A, 3B, 3C, 3D, 3E, 3F, and 3G illustrate a method of manufacturing an electrical interconnection assembly according to an embodiment.

Referring to FIG. 3A, a bonding mask 130 is prepared. The bonding mask 130 includes a flat insulating plate 131 formed of an insulator, and a plurality of first through-holes 132, a plurality of second through-holes 133, and a plurality of third through-holes 134 formed in the flat insulating plate 131. The plurality of first through-holes 132 may be formed at positions corresponding to the second ends of the first conductive lines 1115 of the circuit boards 1110. The plurality of second through-holes 133 and the plurality of third through-holes 134 may be formed at positions corresponding to the second ends of the second conductive lines 1156 of the circuit boards 1110.

Figure 3B:
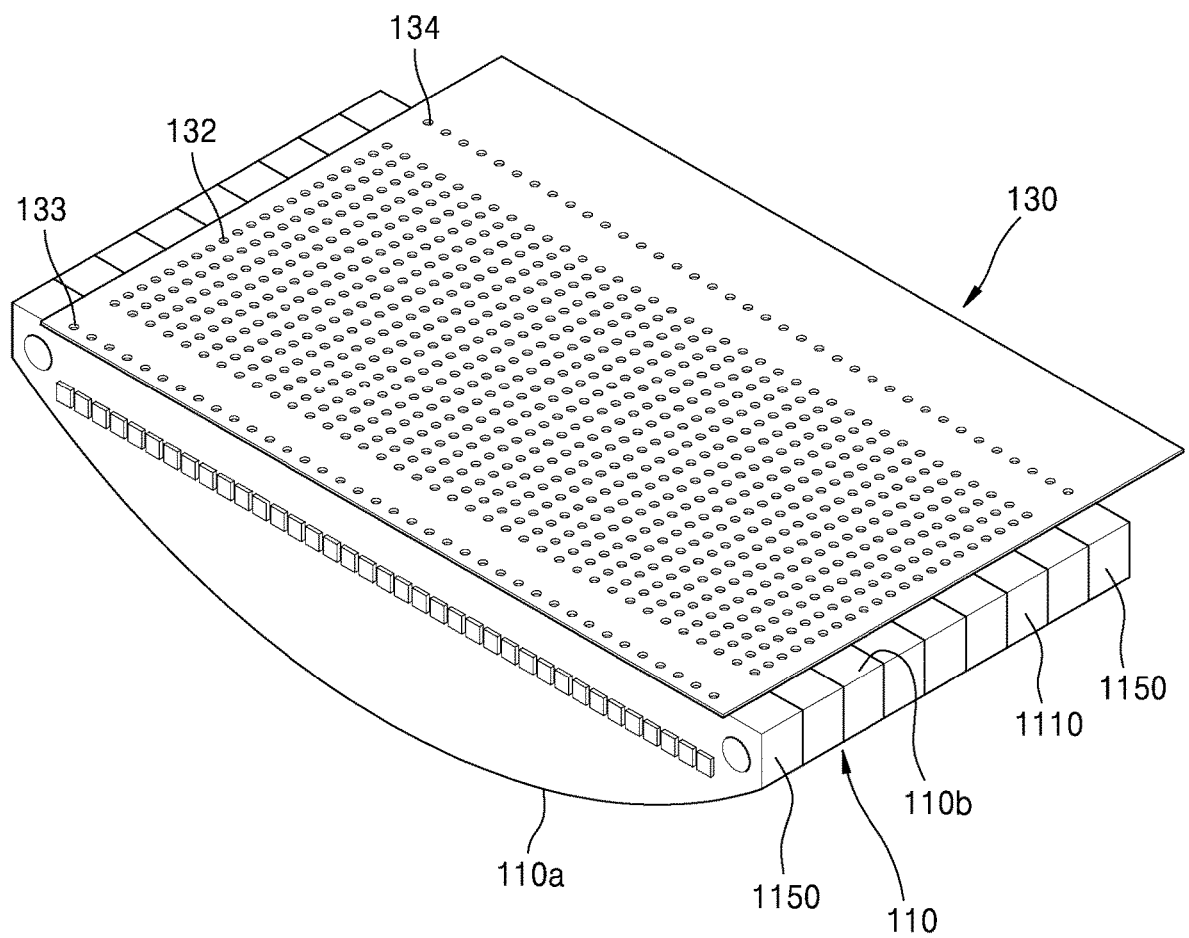
Figure 3C:
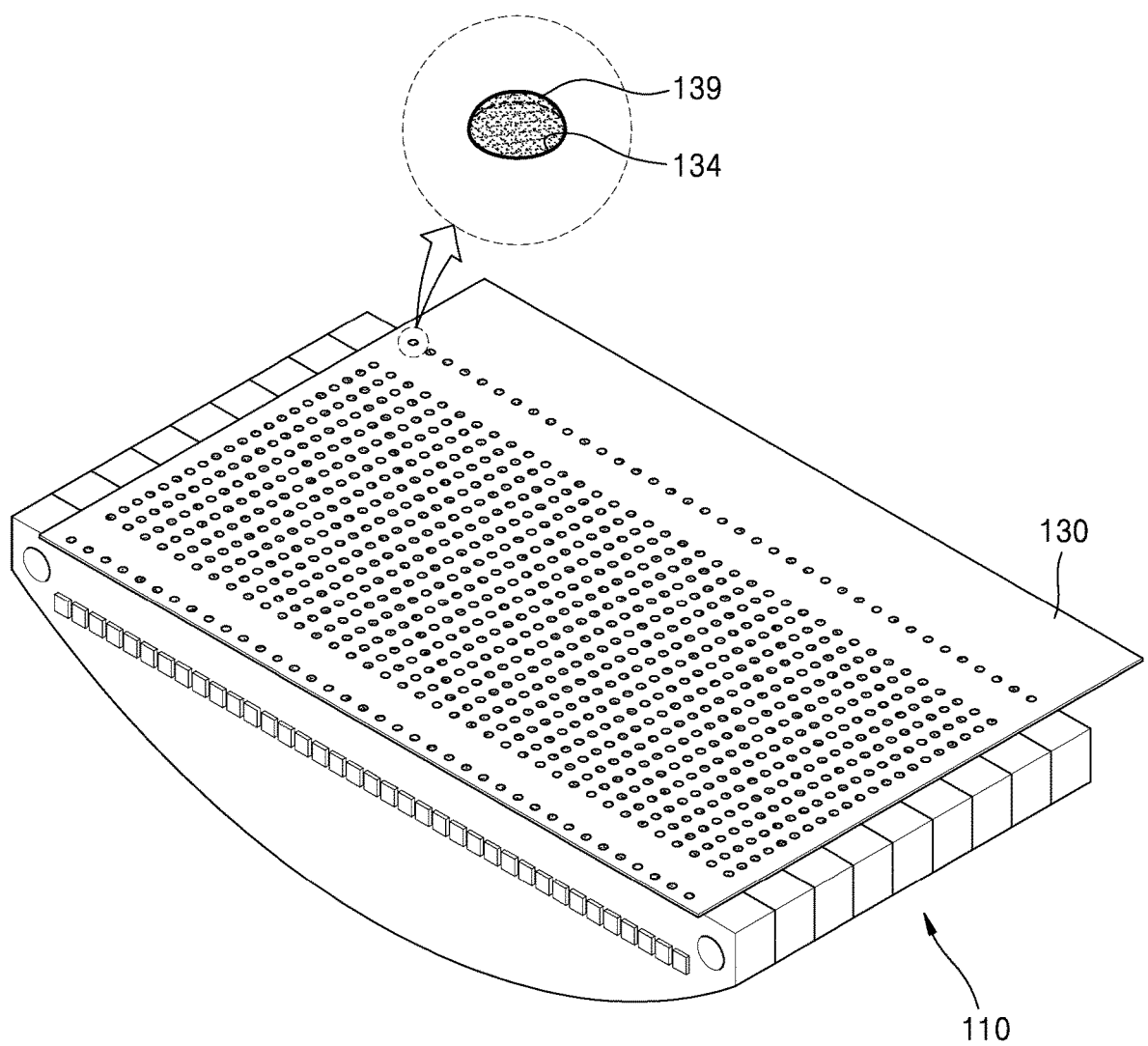

Subsequently, as shown in FIGS. 3B and 3C, the bonding mask 130 is placed on the lower surface 110b of the interposer 110, and the plurality of first to third through-holes 132, 133, and 134 of the bonding mask 130 are filled with conductive epoxy 139.

Figure 3D:
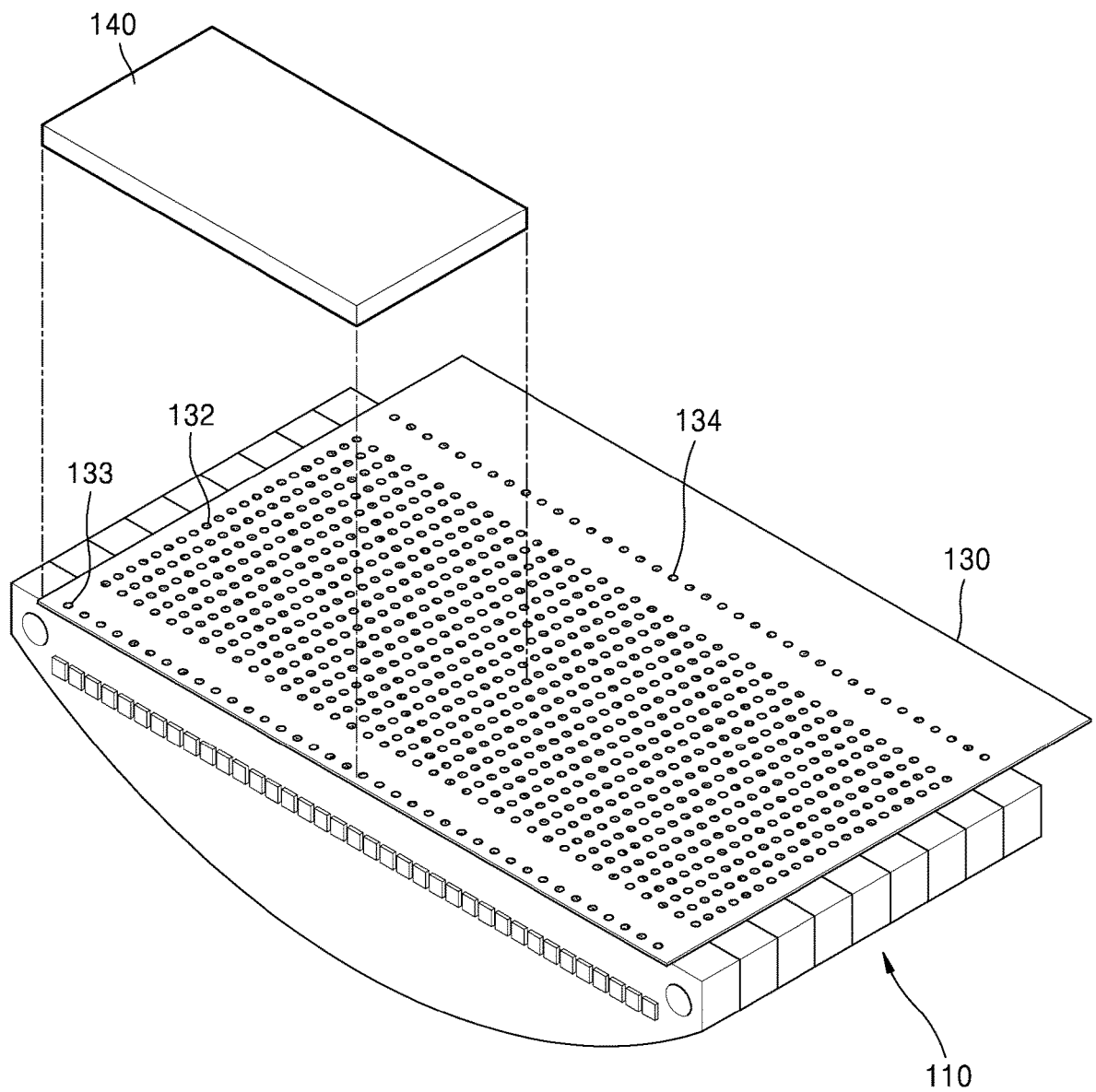
Figure 3E:
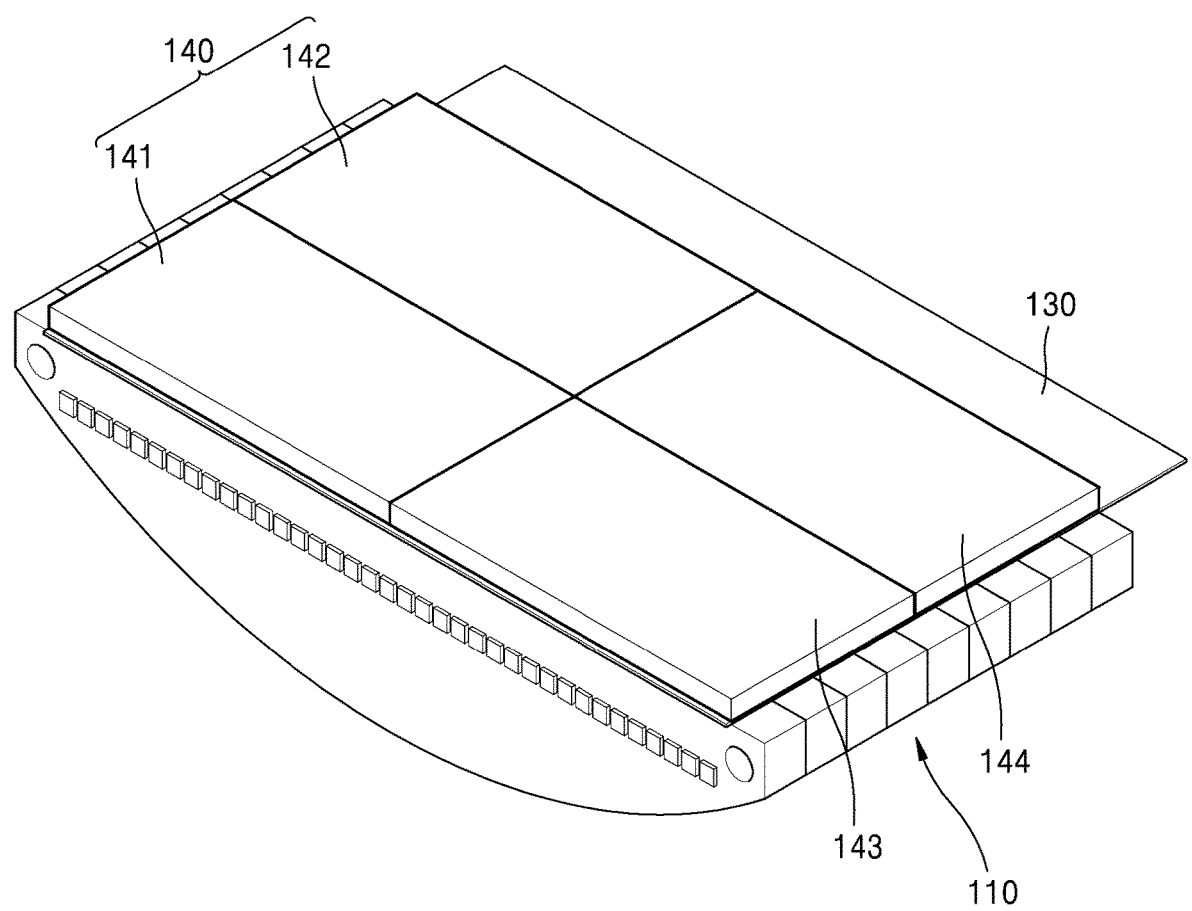

Subsequently, as shown in FIGS. 3D and 3E, an integrated circuit chip 140 is attached to the bonding mask 130. As described above, the integrated circuit chip 140 has a surface-mounted package in which electrode terminals are arranged on a flat plate surface. Thus, the integrated circuit chip 140 is electrically connected to the first and second conductive lines 1115 and 1156 and also bonded to the bonding mask 130 through the conductive epoxy 139 with which the plurality of first to third through-holes 132, 133, and 134 are filled. In this case, the bonding mask 130 and the integrated circuit chip 140 may be bonded to each other by, for example, a flip-chip-bonding technique. For example, bump balls smaller than the first through third through-holes 132, 133, and 134 of the bonding mask 130 are mounted on the integrated circuit chip 140. When the integrated circuit chip 140 is aligned with the bonding mask 130, the bump balls are inserted into the first through third through-holes 132, 133, and 134 of the bonding mask 130. When the conductive epoxy 139 is cured, the interposer 110 and the integrated circuit chip 140 are bonded to each other.

There may be thousands of piezoelectric elements 171. The piezoelectric elements 171 may be separated into four groups, and four integrated circuit chips 141, 142, 143, and 144 may provide inputs and/or outputs for four groups. It will be appreciated that the number of groups or the circuit chips does not limit an embodiment. In some cases, a single integrated circuit chip 140 may be used to provide inputs and/or outputs of all of the piezoelectric elements 171.

Figure 3F:
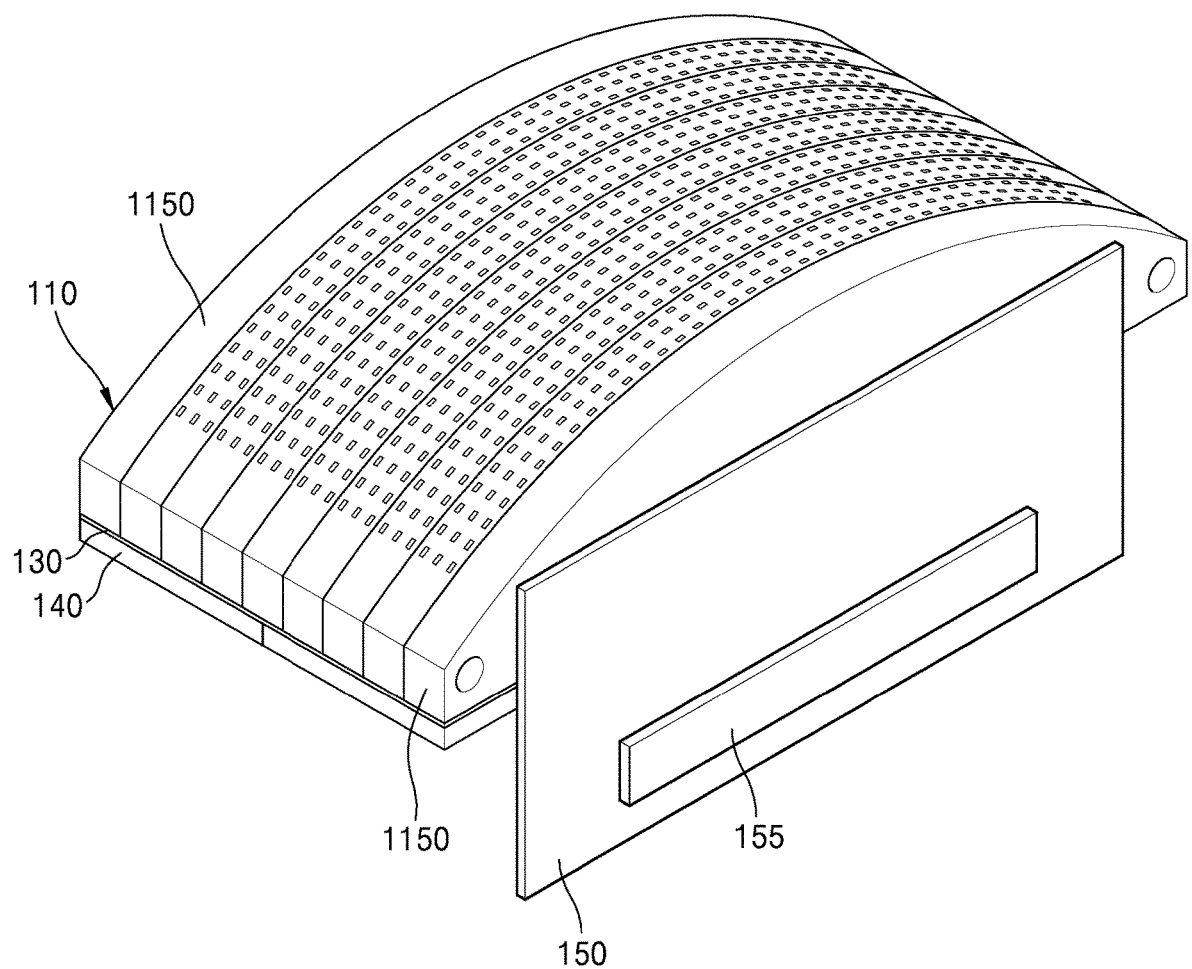

Subsequently, as shown in FIG. 3F, a flexible printed circuit board 150 is attached to an outer side of the interposer 110. The flexible printed circuit board 150 may include an electrode pad 155. The flexible printed circuit board 150 may be in contact with conductive wires of an outwardly extending cable.

Figure 3G:
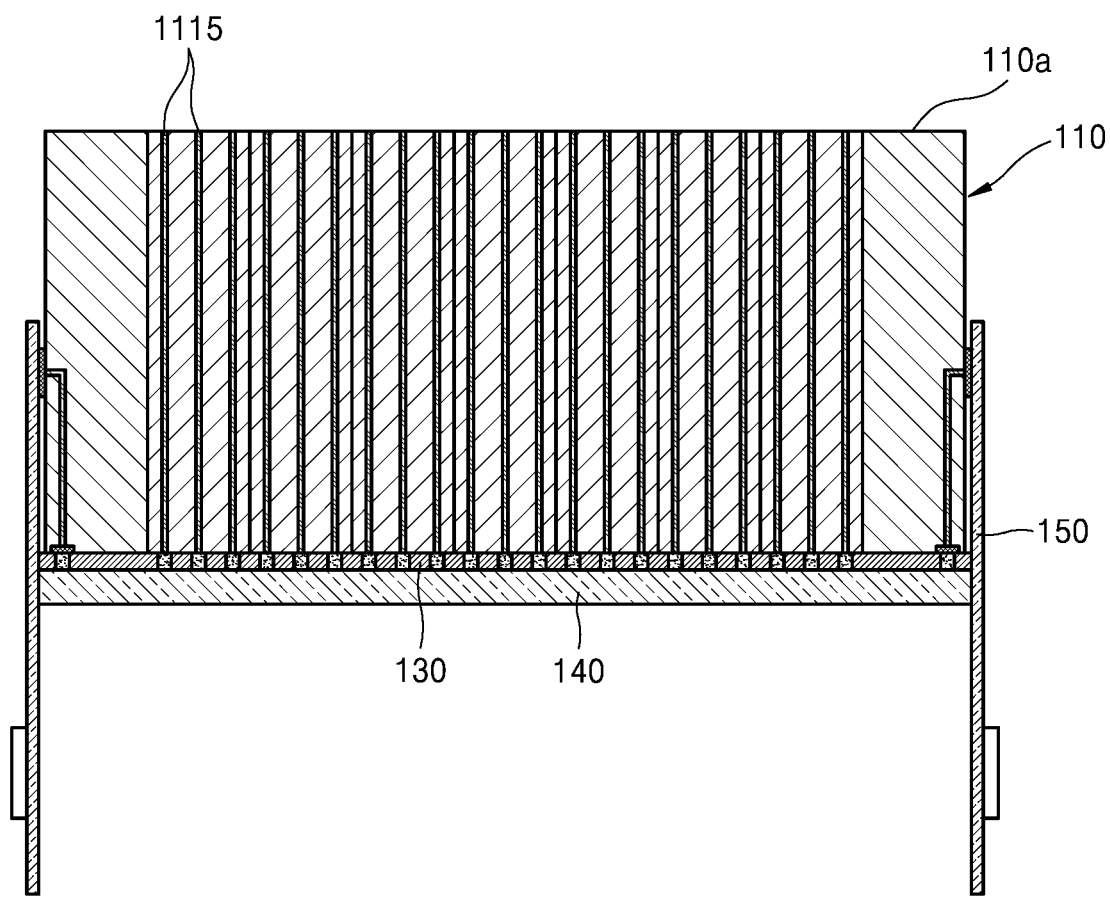

Referring to FIG. 3G, the electrical interconnection assembly is completed by attaching such a flexible printed circuit board 150 to both side surfaces of the interposer 110. The electrical interconnection assembly is attached to the bottom of the 2D acoustic module to perform electrical outputting and inputting for the piezoelectric elements 171.

In the foregoing embodiments, the interposer 110 has been described as an example in which electrode pads 1155 are formed on both sides of the interposer 110. However, it will be appreciated that the outer substrate 1150 may be provided on only one side of the interposer 110 and the electrode pad 1155 may be formed on only one side.

Figure 4A:
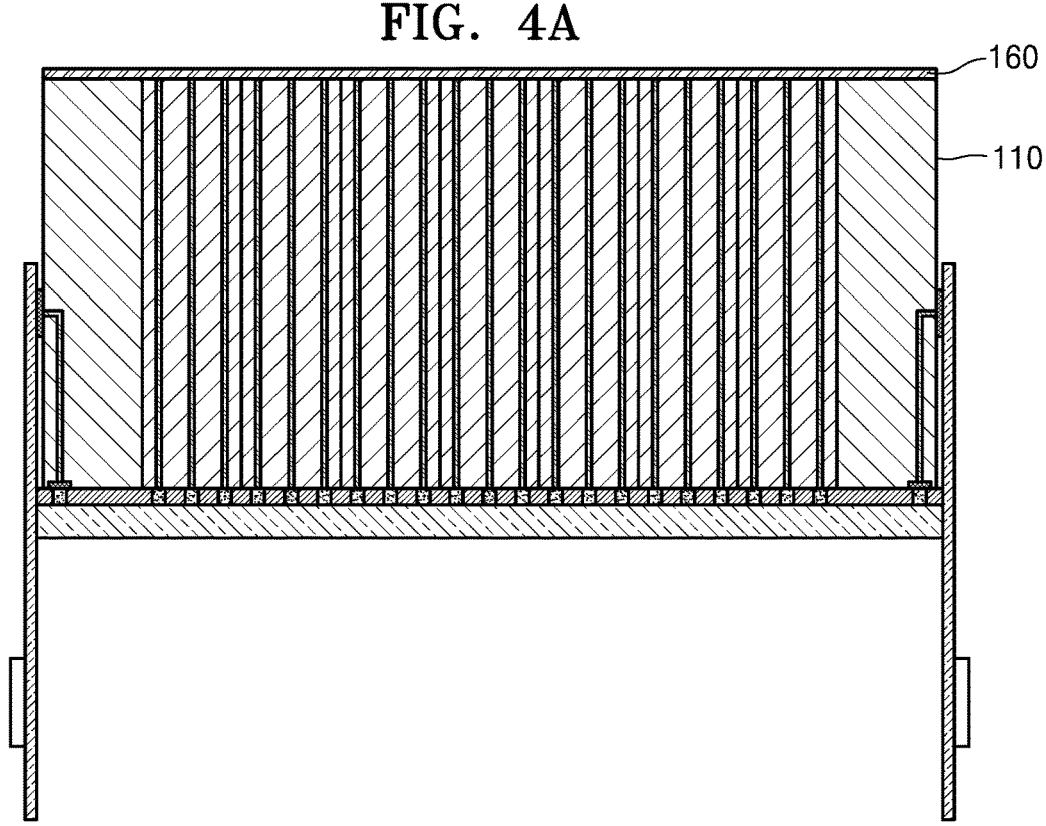
FIGS. 4A, 4B, and 4C illustrate a method of providing a 2D acoustic module in an electrical interconnection assembly according to an embodiment.
Figure 4B:
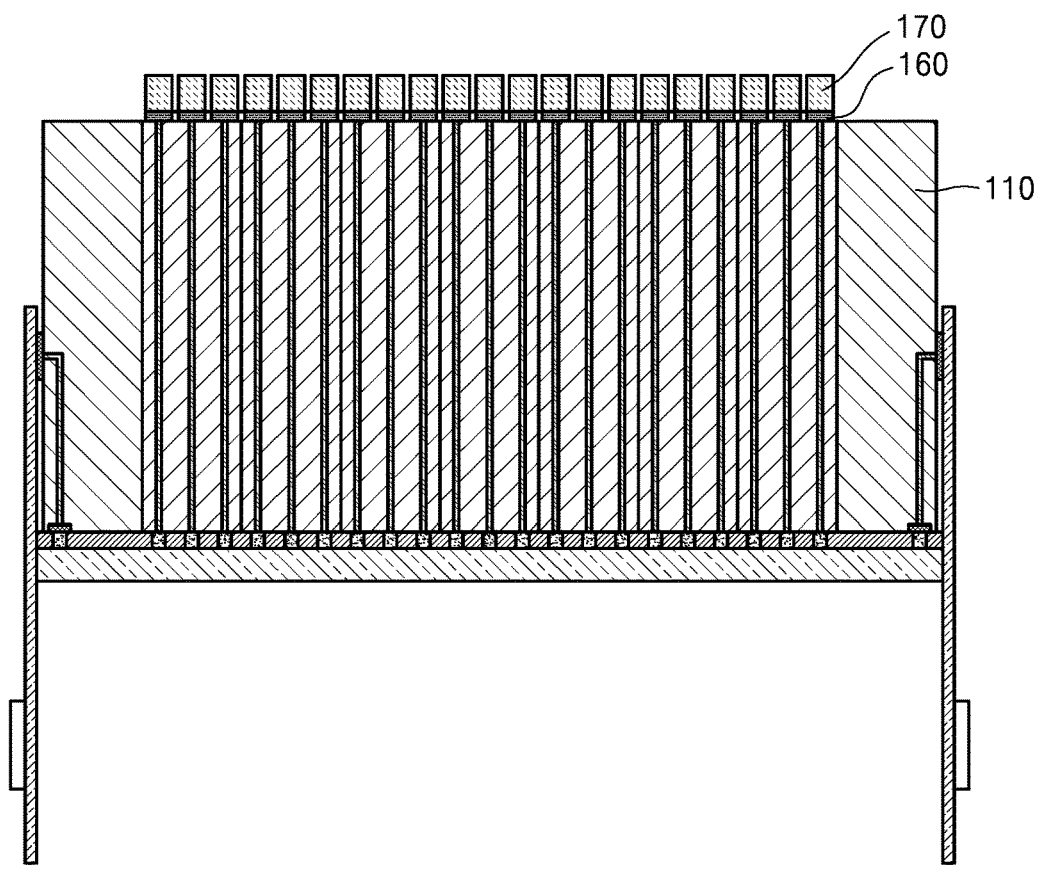
Figure 4C:
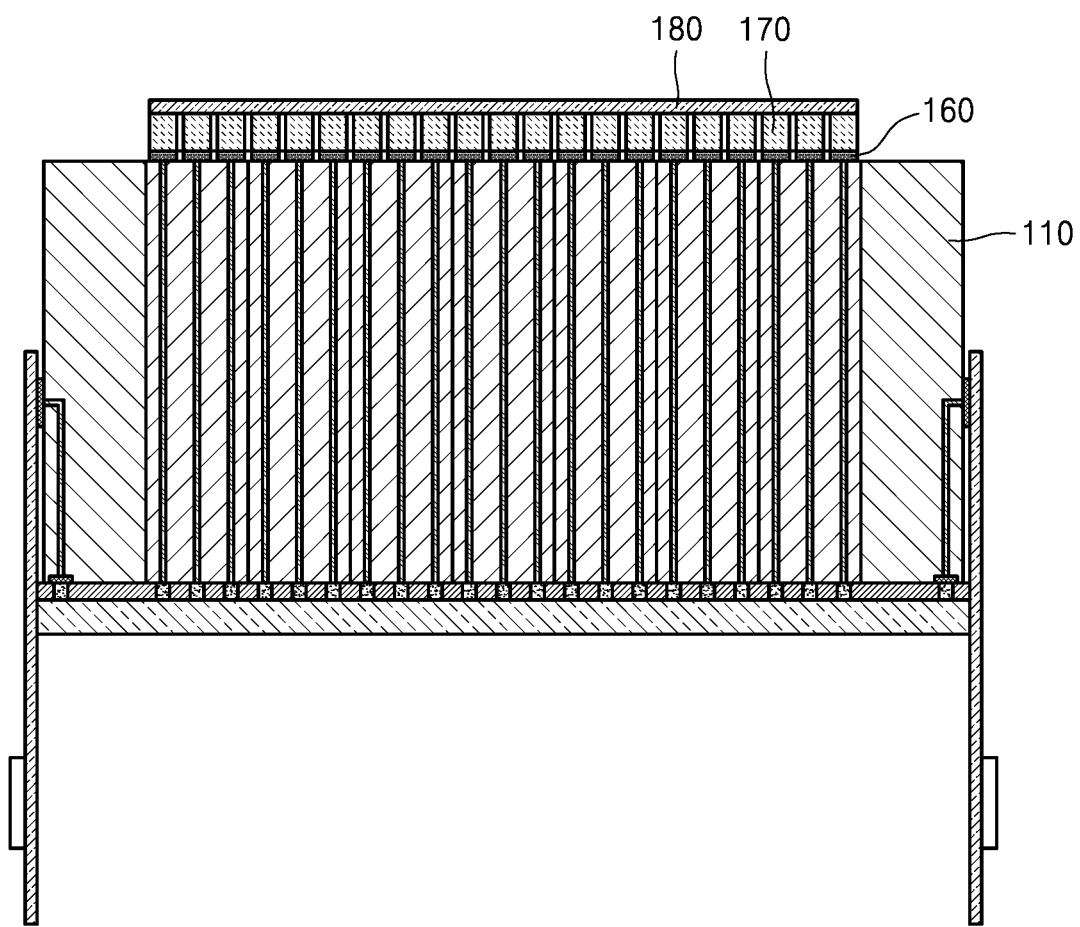

FIGS. 4A to 4C illustrate a method of providing a 2D acoustic module in an electrical interconnection assembly according to an embodiment.

Referring to FIG. 4A, a lower electrode layer 160 made of a conductive material is formed on an upper surface of the interposer 110 of the electrical interconnection assembly.

Subsequently, as shown in FIG. 4B, a piezoelectric layer 170 is formed on the lower electrode layer 160. The lower electrode layer 160 and the piezoelectric layer 170 may be diced to form the piezoelectric elements 171. In an embodiment, the lower electrode layer 160 may be first diced and divided, and then the piezoelectric elements 171 may be attached on the lower electrode layer 160.

Subsequently, referring to FIG. 4C, it is possible to manufacture an ultrasound probe by forming an acoustic matching layer 180 on the piezoelectric layer 170 and forming an acoustic lens layer 190 (refer to FIG. 1) on the acoustic matching layer 180.

Figure 5:
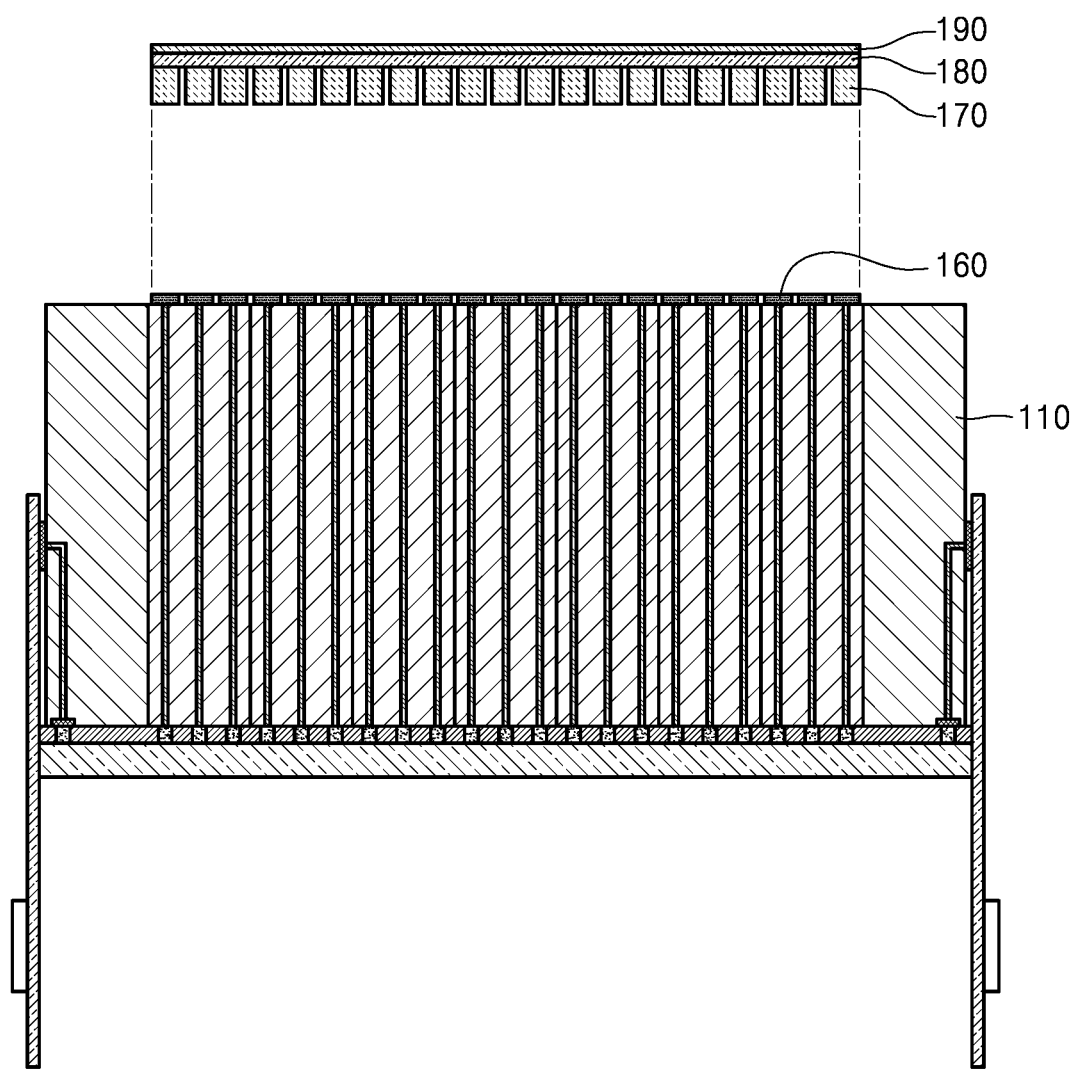
FIG. 5 illustrates a method of providing a 2D acoustic module in an electrical interconnection assembly according to an embodiment.

FIG. 5 illustrates a method of providing a 2D acoustic module in an electrical interconnection assembly according to an embodiment. Referring to FIG. 5, first, a 2D acoustic module including a piezoelectric layer 170 in which piezoelectric elements 171 are divided may be manufactured. Then, the 2D acoustic module may be attached to the electrical interconnection assembly.

Figure 6A:
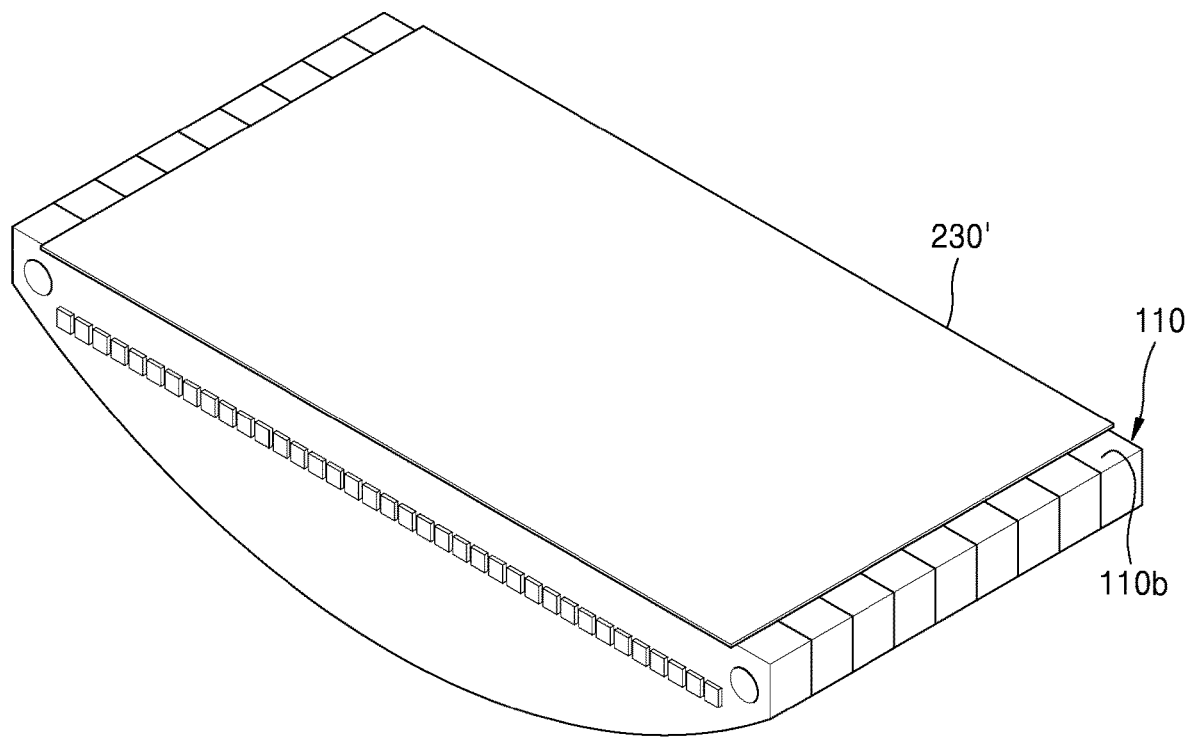
FIGS. 6A, 6B, and 6C illustrate a method of manufacturing a bonding mask according to an embodiment.
Figure 6B:
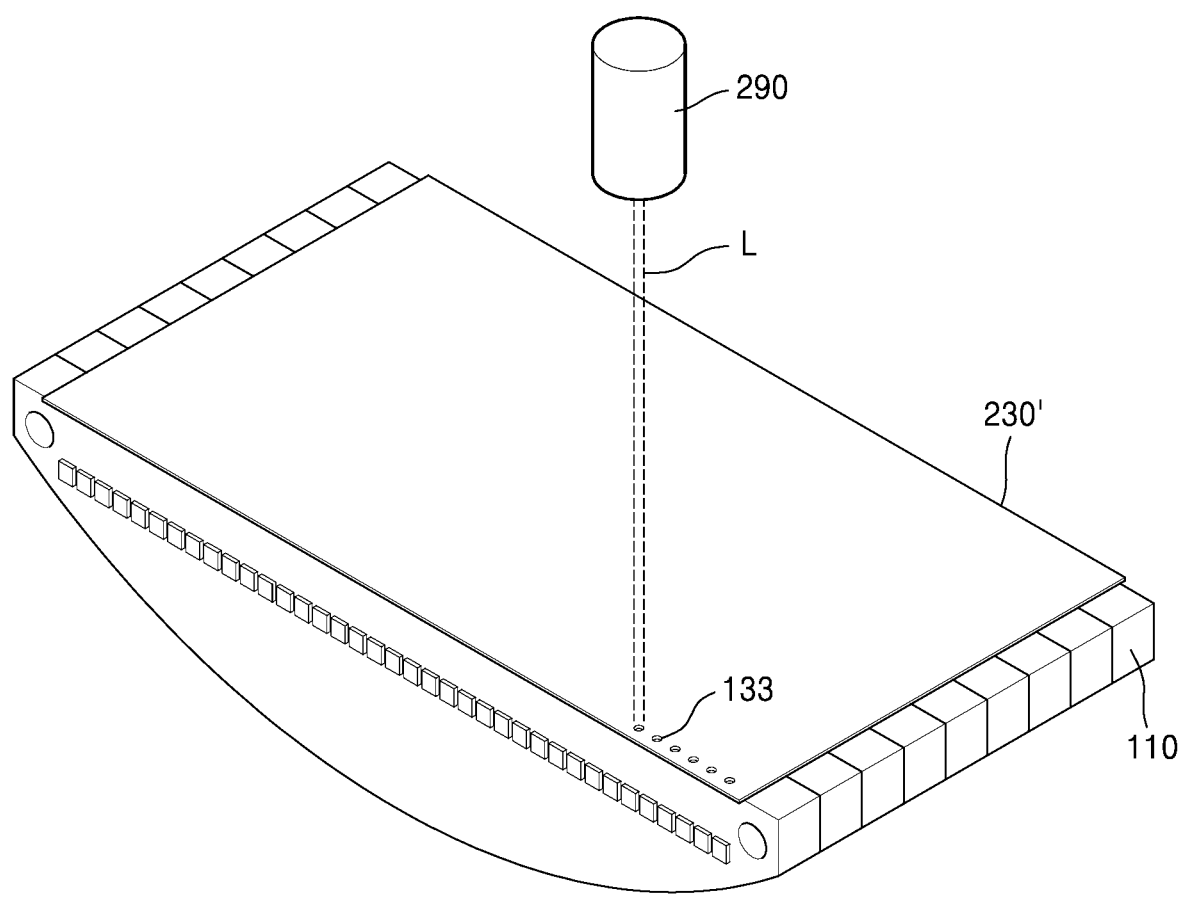
Figure 6C:
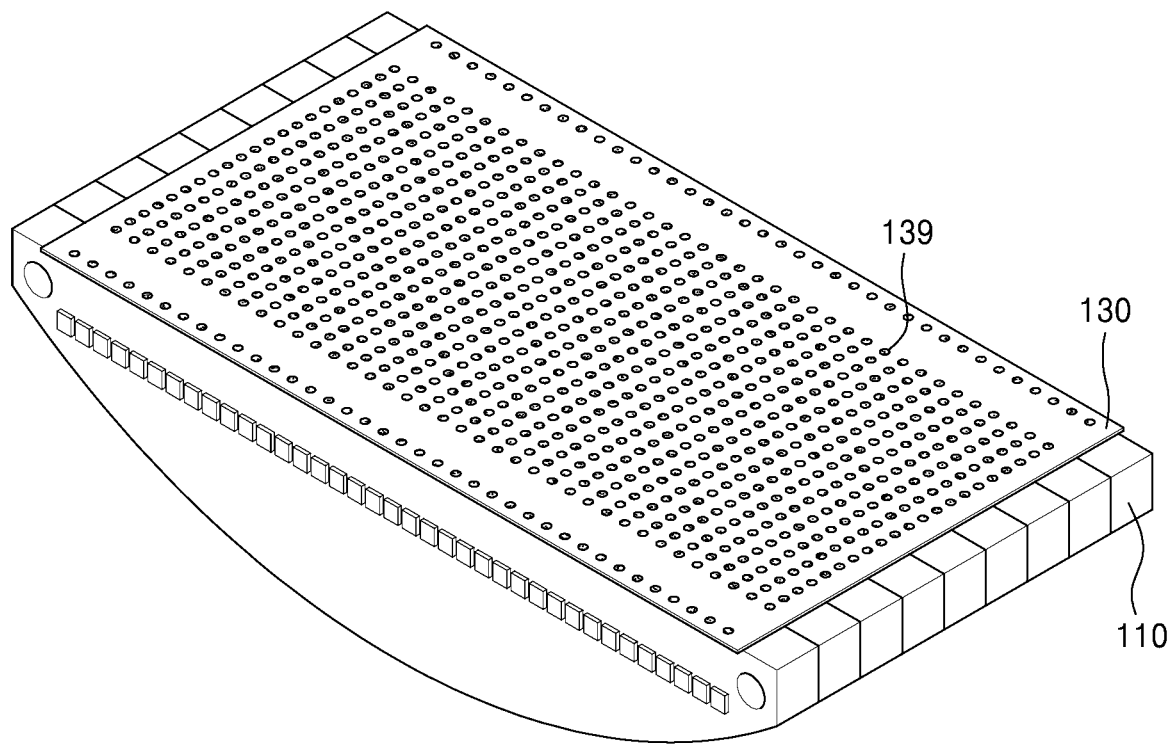

FIGS. 6A to 6C illustrate a method of manufacturing a bonding mask 130 according to an embodiment. Referring to FIG. 6A, first, a film 230' with no through-hole is attached to the lower surface 110b of the interposer 110. When the film 230' is made of a transparent material, it is possible to check positions of the second ends of the first and second conductive lines 1115 and 1156 exposed to the lower surface 110b of the interposer 110.

Subsequently, referring to FIG. 6B, first to third through-holes 132, 133, and 134 are formed at positions of the film 230' corresponding to the second ends of the first and second conductive lines 1115 and 1156 by using a laser light source 290. As a result, the bonding mask 130 is manufactured.

Subsequently, referring to FIG. 6C, the first to third through-holes 132, 133, and 134 of the bonding mask 130 are filled with conductive epoxy 139. Subsequently, as described above with reference to FIGS. 3D and 3E, the integrated circuit chip 140 is attached to the bonding mask 130.

FIGS. 7A to 7E illustrate a method of manufacturing an interposer according to an embodiment.

Figure 7A:
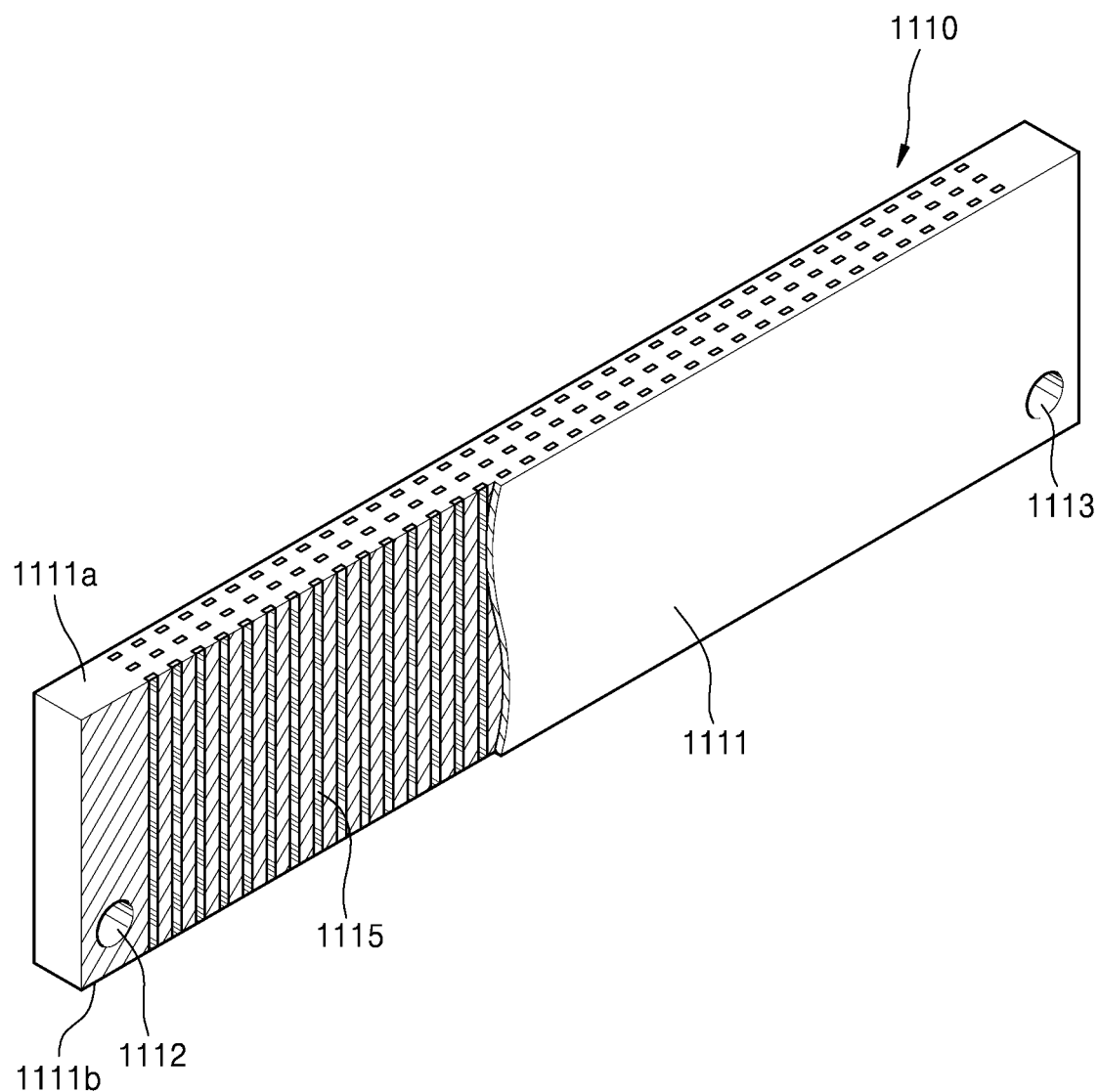
FIGS. 7A, 7B, 7C, 7D, and 7E illustrate a method of manufacturing an interposer according to an embodiment.

Referring to FIG. 7A, a plurality of circuit boards 1110 are prepared. Each of the circuit boards 1110 includes an insulator 1111 with a flat plate shape and guide holes 1112 and 1113, and are substantially the same as described above with reference to FIGS. 2A and 2B. As can be seen in a partial sectional view of FIG. 7A, first conductive lines 1115 are provided inside the insulator 1111 and arranged in at least one column. Both of a first side portion 1111a and a second side portion 1111b of the insulator 1111 may have a flat plate shape.

Because the first side portion 1111a has a flat plate shape, the piezoelectric layer 170 also has a flat plate shape.

Figure 7B:
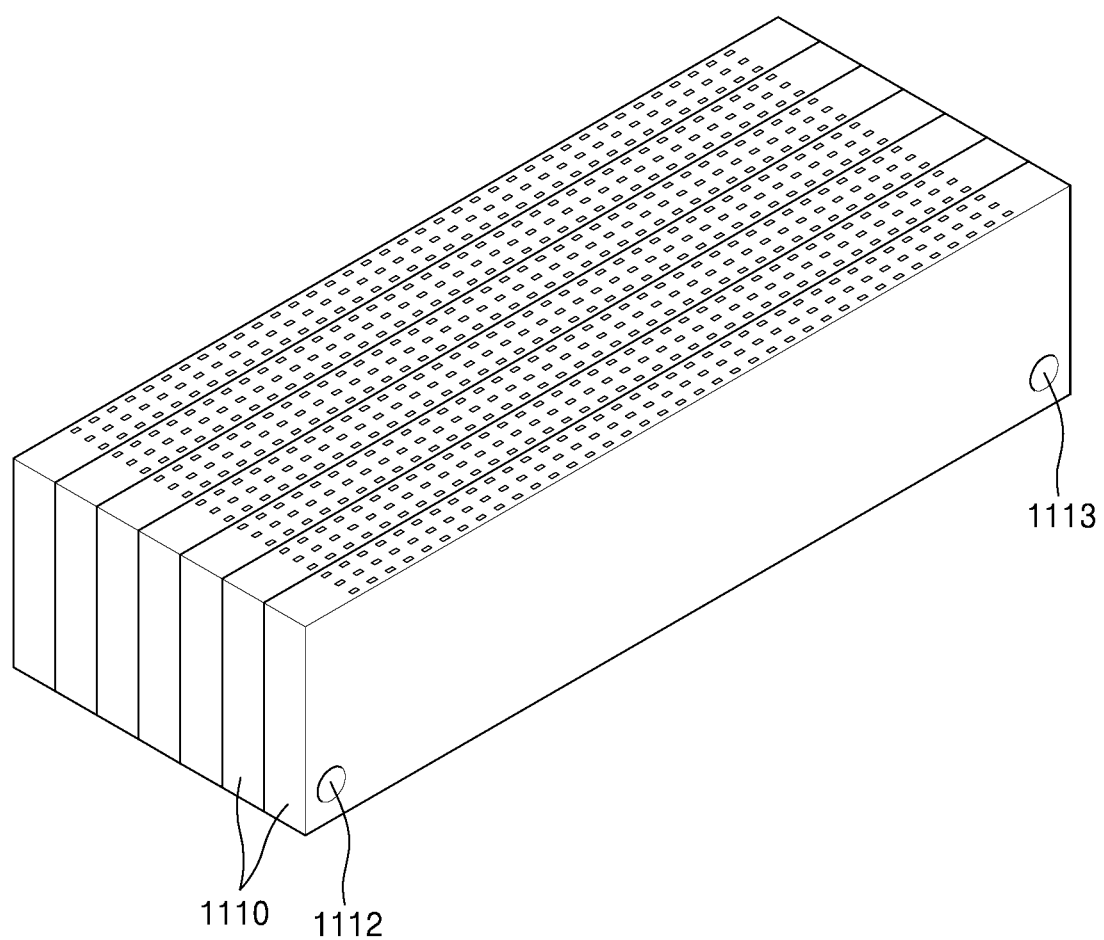

Referring to FIG. 7B, the circuit boards 1110 are stacked such that the first side portions 1111a are coplanar with each other and the second side portions 1111b are coplanar with each other. It is possible to facilitate the arrangement of the circuit boards 1110 during the stacking process by using the guide holes 1112 and 1113. As described above with reference to FIGS. 2D and 2E, it is possible to facilitate thickness adjustment while the circuit boards 1110 are stacked by interposing a film 1120 therebetween.

Figure 7C:
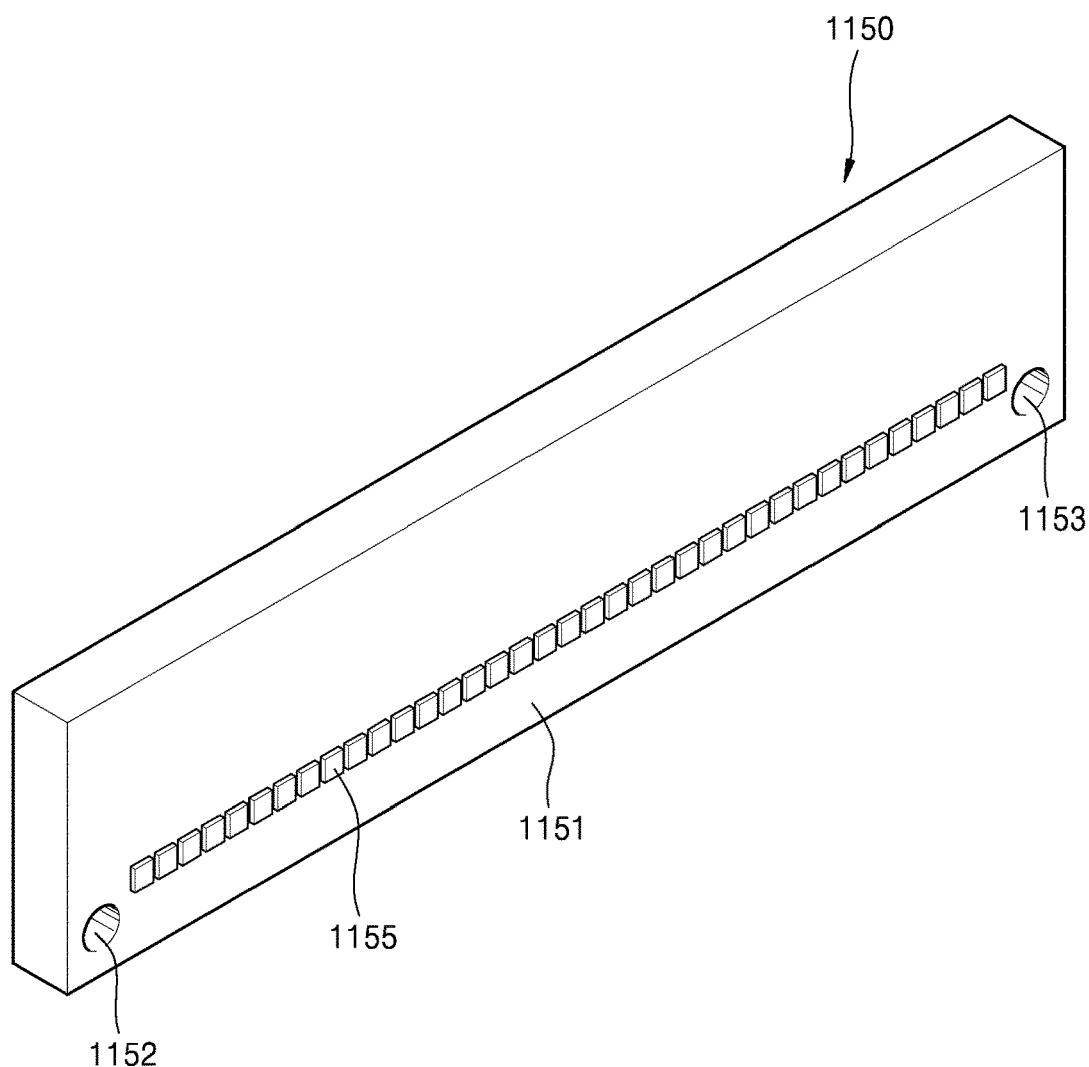
Figure 7D:
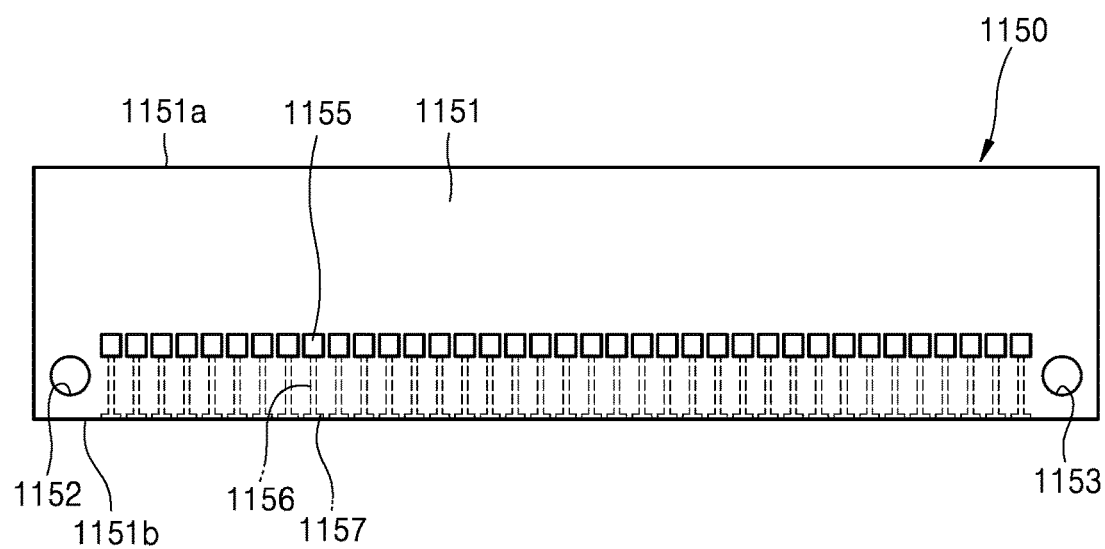

Referring to FIGS. 7C and 7D, an outer substrate 1150 is prepared. The outer substrate 1150 has the same external shape as the circuit boards 1110. Second conductive lines 1156 are located inside the outer substrate 1150. First ends of the second conductive lines 1156 are exposed to an outer flat plate surface of the outer substrate 1150, and the second ends of the second conductive lines 1156 are exposed to a second side portion 1111b. At the first ends of the second conductive lines 1156 exposed to the outer flat plate surface of the outer substrate 1150, electrode pads 1155 may be formed to facilitate electrical interconnection. Also, at the second ends of the second conductive lines 1156 exposed to the second side portion 1111b, terminals or pads 1157 may be formed to facilitate electrical interconnection.

Figure 7E:
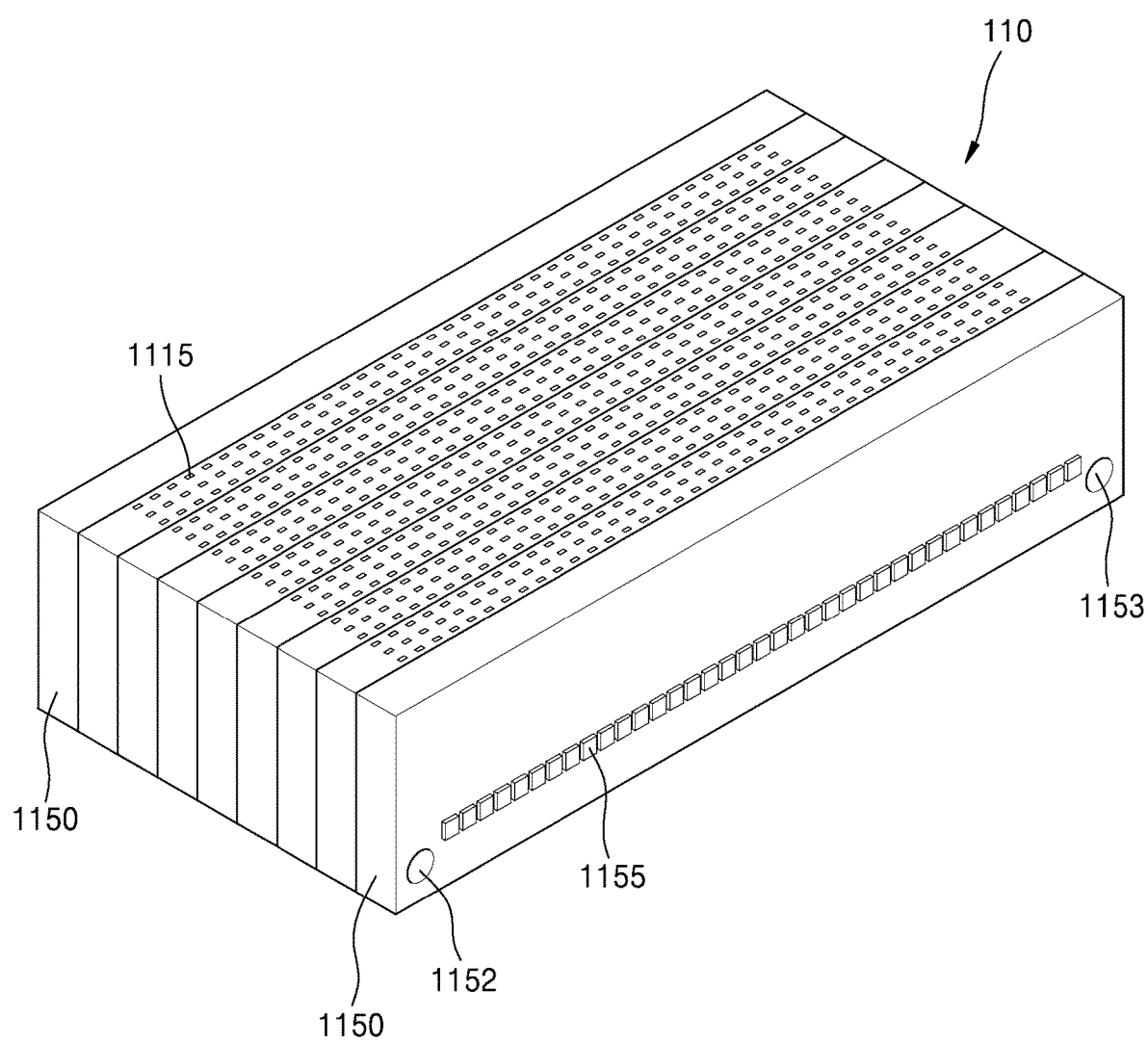

FIG. 7E shows a complete configuration of an interposer 110 in which outer substrates 1150 are placed at both outer sides of a stack structure of the circuit boards 1110. The outer substrates 1150 may have a horizontally symmetrical structure, but are not limited thereto.

Figure 8A:
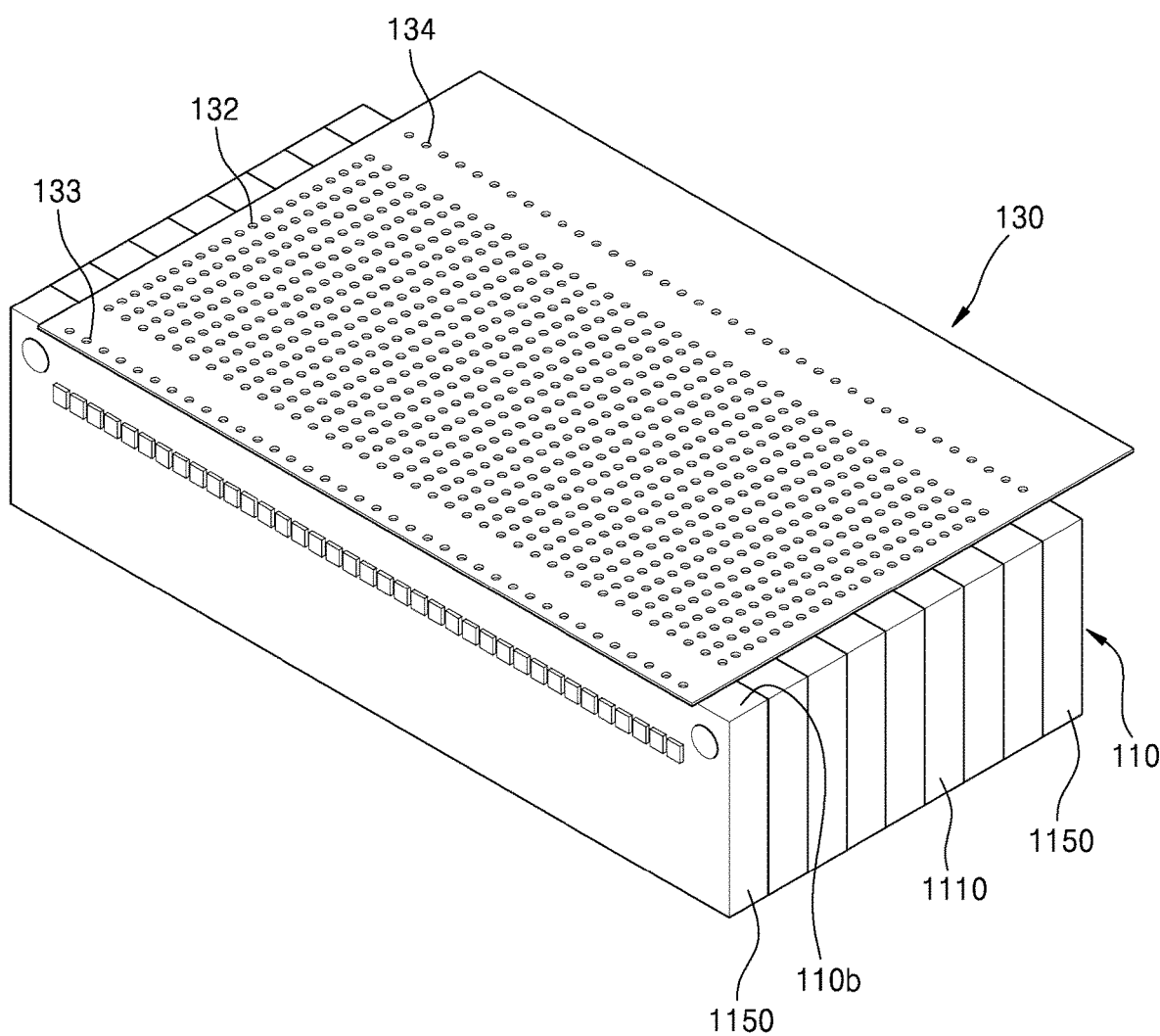
FIGS. 8A, 8B, and 8C illustrate a method of manufacturing an electrical interconnection assembly according to an embodiment.
Figure 8B:
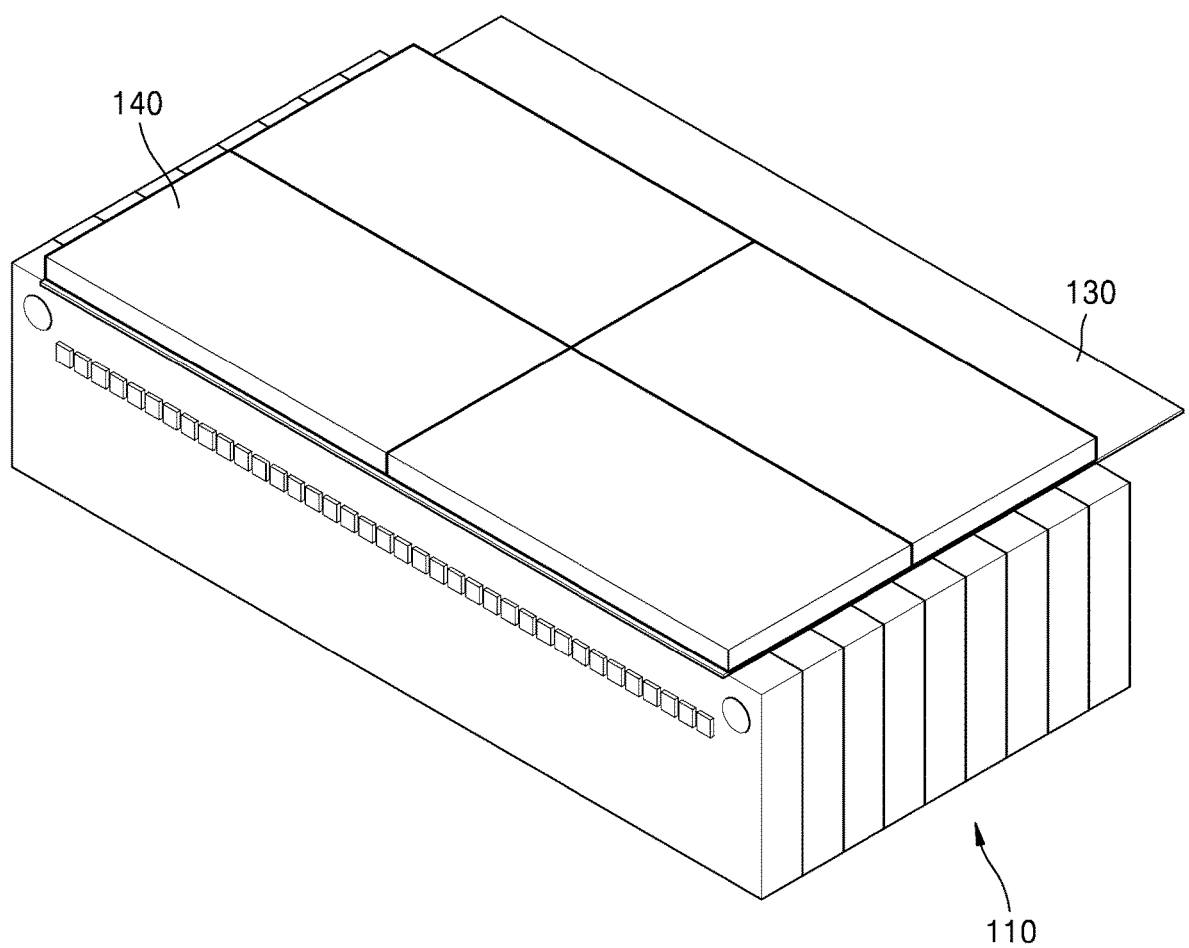
Figure 8C:
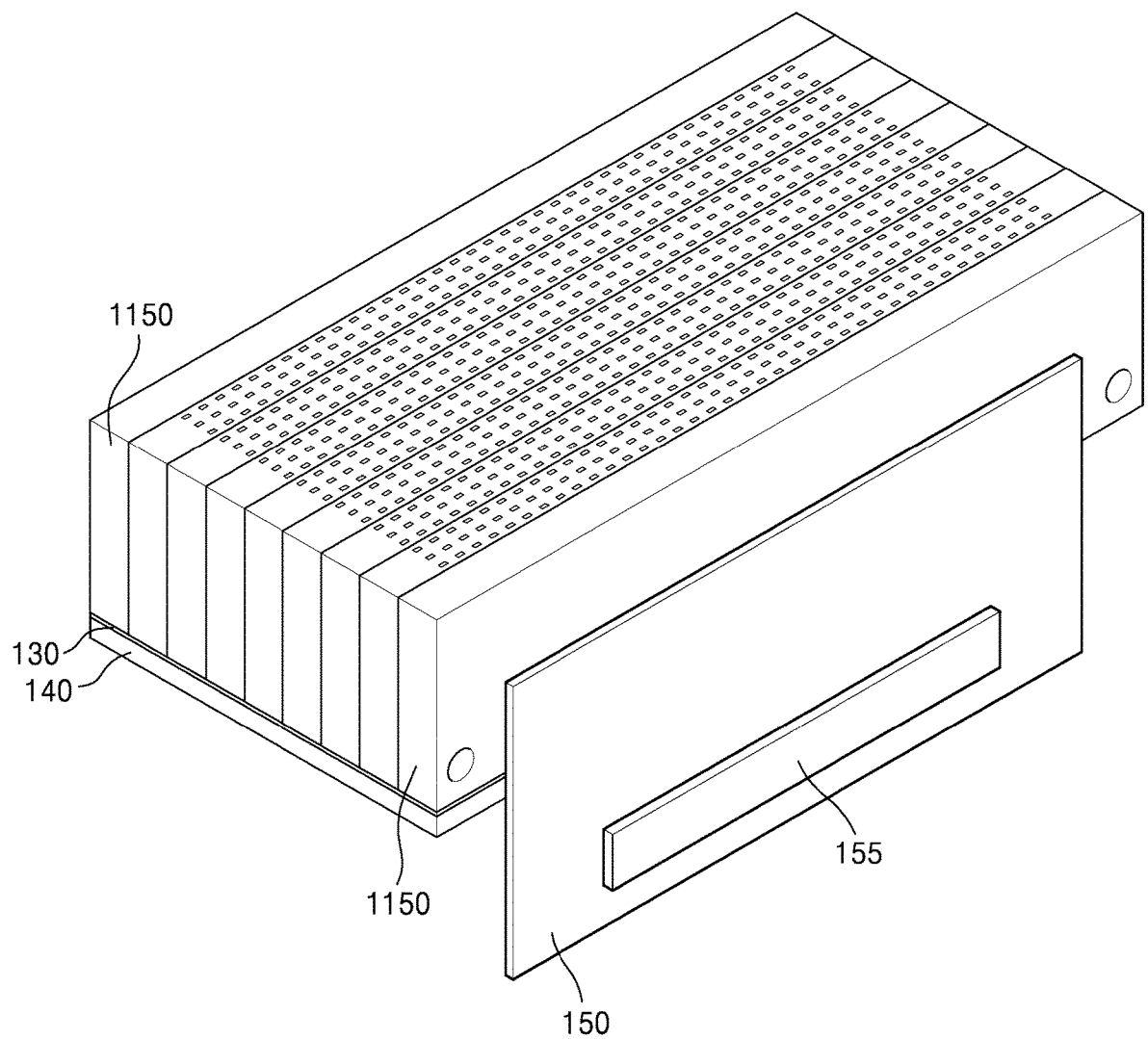

FIGS. 8A to 8C illustrate a method of manufacturing an electrical interconnection assembly according to an embodiment.

Referring to FIG. 8A, a bonding mask 130 is placed on a lower surface 110b of an interposer 110. The bonding mask 130 includes a flat insulating plate 131 formed of an insulator and a plurality of first to third through-holes 132, 133, and 134. Subsequently, the plurality of first to third through-holes 132, 133, and 134 of the bonding mask 130 are filled with conductive epoxy 139 (refer to FIG. 3C).

Subsequently, as shown in FIG. 8B, an integrated circuit chip 140 is attached to the bonding mask 130. As described above, the integrated circuit chip 140 has a surface-mounted package in which electrode terminals are arranged on a flat plate surface. Thus, the integrated circuit chip 140 is electrically connected to first and second conductive lines of the interposer 110 and also bonded to the bonding mask 130 through the conductive epoxy 139 with which the plurality of first to third through-holes 132, 133, and 134 are filled.

Next, as shown in FIG. 8C, a flexible printed circuit board 150 is attached to an outer side of the interposer 110. The flexible printed circuit board 150 may include an electrode pad 155. The flexible printed circuit board 150 may be in contact with conductive wires of an outwardly extending cable.

Referring back to FIG. 3G, the electrical interconnection assembly is completed by attaching such a flexible printed circuit board 150 to both side surfaces of the interposer 110. The electrical interconnection assembly is attached to the bottom of a 2D acoustic module to perform electrical outputting and inputting for piezoelectric elements 171.

Figure 9:
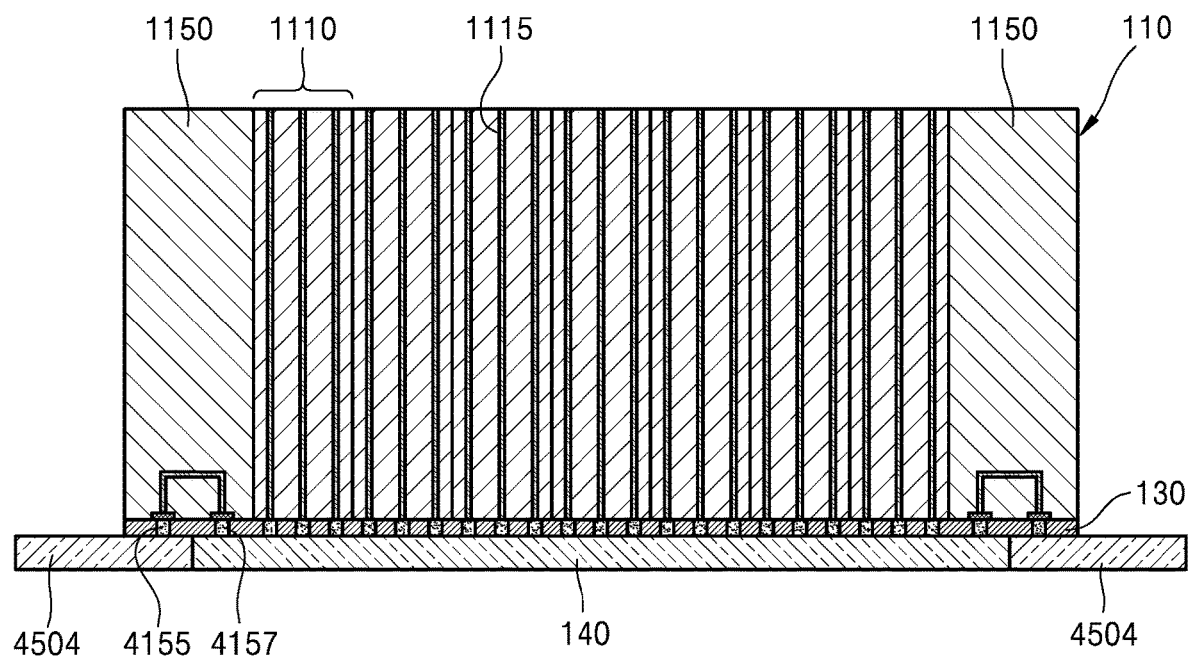
FIG. 9 is a schematic sectional view of an electrical interconnection assembly according to an embodiment.

FIG. 9 is a schematic sectional view of an electrical interconnection assembly according to still an embodiment. Referring to FIG. 9, electrode pads 4155 for external wirings together with pads 4157 for wirings with the integrated circuit chip 140 may be provided at lower end side portions, rather than outer side surfaces, of outer substrates 1150 of an interposer 110. In this case, a flexible printed circuit board 4504 is in contact with the lower end side portions of the outer substrates 1150 to make electrical wiring.

Figure 10:
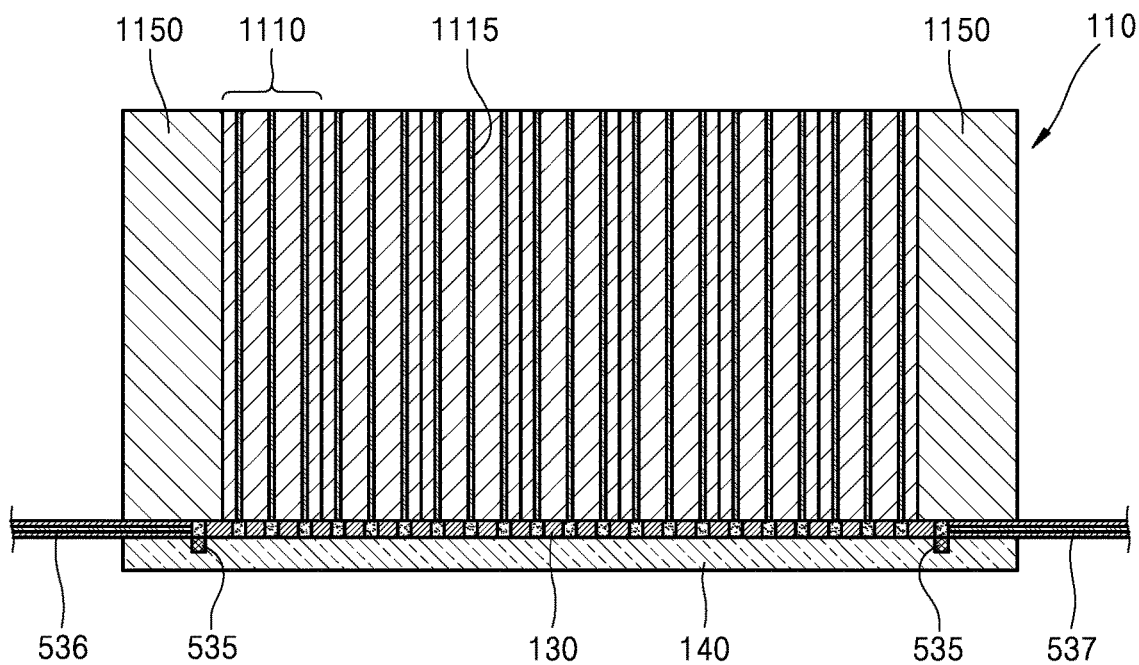
FIG. 10 is a schematic sectional view of an electrical interconnection assembly according to an embodiment.

FIG. 10 is a schematic sectional view of an electrical interconnection assembly according to yet an embodiment. Referring to FIG. 10, the outer substrates 1150 are placed at an outer side of an interposer 110, and pattern wiring lines 536 and 537 are inserted into a bonding mask 130 so that second terminals 535 for transmitting and receiving electrical signals to and from the outside in order to power on, and control, the integrated circuit chip 140 may be electrically connected to the outside.

Alternatively, the second terminals 535 for transmitting and receiving electrical signals to and from the outside in order to power on, and control, the integrated circuit chip 140 may be exposed and connected to a flexible printed circuit board through wire bonding.

Figure 11:
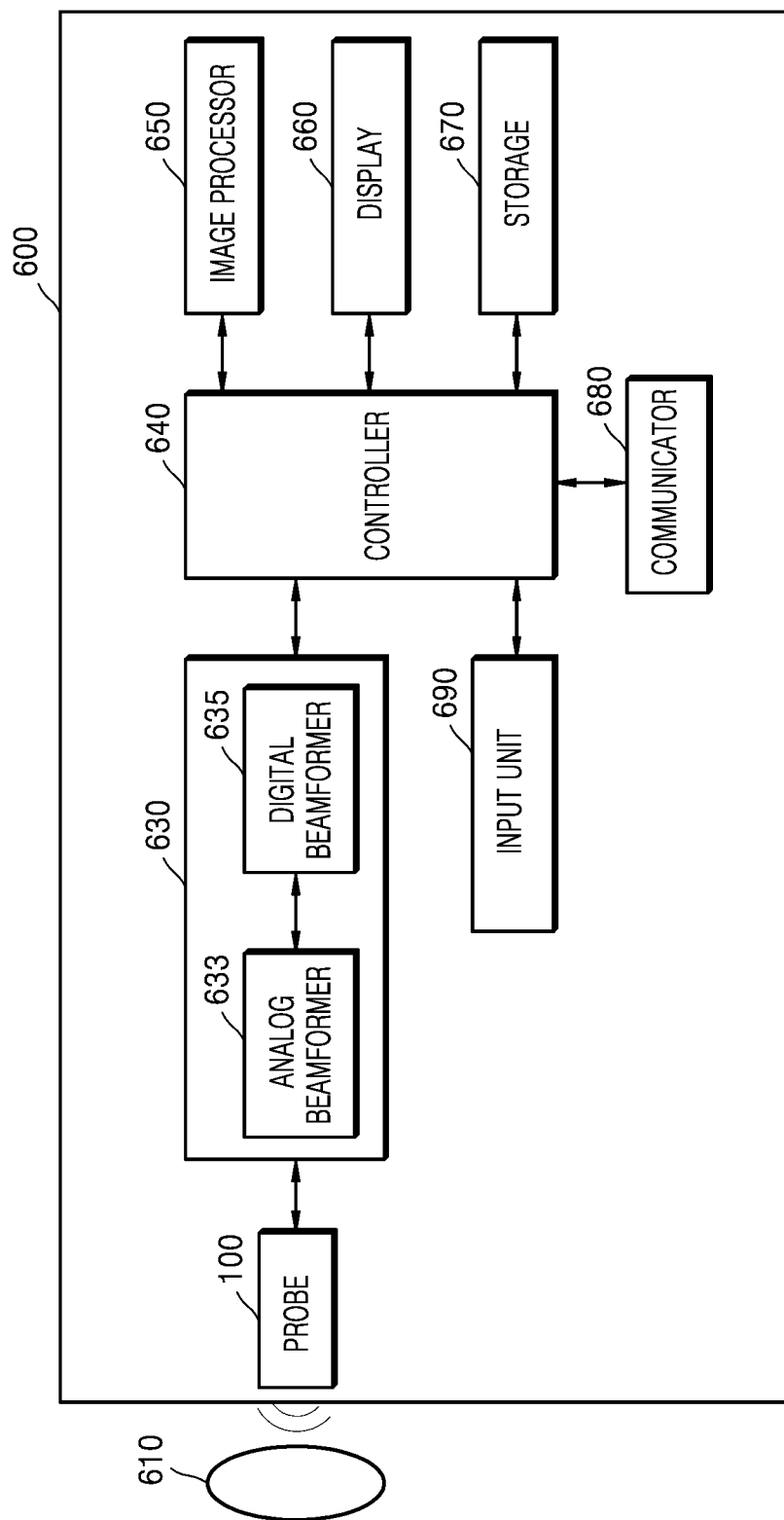
FIG. 11 is a block diagram showing a configuration of an ultrasound diagnostic apparatus according to an embodiment.

FIG. 11 is a block diagram showing a configuration of an ultrasound diagnostic apparatus 600 according to an embodiment. Referring to FIG. 11, the ultrasound diagnostic apparatus 600 may include an ultrasound probe 100, an ultrasound transceiver 630, a controller 640, an image processor 650, a display 660, an input unit 690, a storage 670, and a communicator 680.

The ultrasound probe 100 may be a 2D probe that is manufactured by the aforementioned embodiments. Also, the ultrasound transceiver 630 may include an analog beamformer 633 and a digital beamformer 635. The ultrasound transceiver 630 and the ultrasound probe 100 are shown as being separate components in FIG. 11. The ultrasound probe 100 according to an embodiment may include some or all elements of the ultrasound transceiver 630. For example, the ultrasound probe 100 may include one or both of the analog beamformer 633 and the digital beamformer 635.

The controller 640 may calculate a time delay value for digital beamforming for each of a plurality of sub-arrays included in a 2D transducer array. Also, the controller 640 may calculate a time delay value for analog beamforming for each transducer included in any one of the plurality of sub-arrays. The controller 640 may control the analog beamformer 633 and the digital beamformer 635 to form transmission signals to be applied to each of a plurality of transducers according to the time delay value for analog beamforming and the time delay value for digital beamforming. The controller 640 may control the analog beamformer 633 to add signals received from the plurality of transducers on a sub-array basis according to the time delay value for analog beamforming. Also, the controller 640 may control the ultrasound transceiver 630 to perform analog-to-digital conversion on the signals added on a sub-array basis. Also, the controller 640 may control the digital beamformer 635 to add digitally converted signals according to the time delay value for digital beamforming to generate ultrasound data. The ultrasound probe 100 according to an embodiment may include some or all elements of the controller 640.

The image processor 650 may generate an ultrasound image using the generated ultrasound data.

The display 660 may display the generated ultrasound image and a variety of information processed by the ultrasound diagnostic apparatus 600. The ultrasound diagnostic apparatus 600 may include one or a plurality of displays 660. Also, the display 660 may be combined with a touch panel and implemented as a touch screen and may provide an input and/or an output functionality.

The controller 640 may control an overall operation of the ultrasound diagnostic apparatus 600 and also control a signal flow between the components of the ultrasound diagnostic apparatus 600. The controller 640 may include a processor configured to process data or programs for performing functions of the ultrasound diagnostic apparatus 600. Also, the controller 640 may receive a control signal from the input unit 690 or an external apparatus to control operation of the ultrasound diagnostic apparatus 600.

The ultrasound diagnostic apparatus 600 may include the communicator 680 and may be connected to an external apparatus such as a server, a medical device, or a portable device (e.g., a smartphone, a tablet computer, a wearable device, or the like) through the communicator 680.

The communicator 680 may include one or more elements capable of communicating with an external apparatus. For example, the communicator 680 may include at least one of a short-range communication module, a wired communication module, and a wireless communication module.

The communicator 680 may transmit and receive data and control signals to and from an external apparatus.

The storage 670 may store ultrasound images, ultrasound data that is input or to be output, and various programs or data for driving and controlling the ultrasound diagnostic apparatus 600.

The input unit 690 may receive a user input for controlling the ultrasound diagnostic apparatus 600. For example, the user input may include, but is not limited to, an input for manipulating a button, a keypad, a mouse, a trackball, a jog switch, a knob, etc., an input for touching a touch pad or a touch screen, a voice input, a motion input, a biometric information input (e.g., iris recognition, fingerprint recognition, etc.), and the like.

By using the interposer according to the embodiments, it is possible for the ultrasound probe according to the embodiments to connect the transducer elements in the central region in addition to the transducer elements in the peripheral region.

In the method of manufacturing an interposer according to the embodiments, by stacking printed circuit boards (PCBs), e.g., the circuit boards 1110, to manufacture an interposer and also facilitating connection with peripheries such as an integrated circuit chip, a connector, a cable, and the like, it is possible to accomplish cost reduction, process unification and simplification, and structure simplification.

The method of bonding an interposer and an integrated circuit chip and an ultrasound probe using the method according to the present disclosure have been described with reference to the embodiments shown in the drawings for only illustrative purposes in order to facilitate an understanding thereof. Therefore, it will be understood by those skilled in the art that various changes and equivalents thereof may be made. Accordingly, the technical scope of the present disclosure should be determined only by the appended claims.

What is claimed is:

1. A method comprising:
   preparing an interposer, the preparing comprising:
      forming a plurality of first conductive lines in an insulator, wherein first ends of the plurality of first conductive lines are exposed through the insulator to a first surface of the insulator and second ends of the plurality of first conductive lines are exposed through the insulator to a second surface of the insulator that is opposite to the first surface of the insulator;
      forming a plurality of second conductive lines in the insulator, wherein first ends of the plurality of second conductive lines are exposed through the insulator to a side surface of the insulator, the side surface extending from the first surface of the insulator to the second surface of the insulator, and wherein second ends of the plurality of second conductive lines are exposed through the insulator to the second surface of the insulator;
   placing a bonding mask on the second surface of the insulator;
   forming through-holes on the bonding mask;
   filling the through-holes with a conductive material; and
   bonding an integrated circuit chip to the bonding mask,
   wherein the forming the through-holes further comprises:
      after the placing the bonding mask on the insulator, forming the through-holes on the bonding mask by laser emission, and
   wherein the bonding mask includes a transparent film.

2. The method of claim 1, wherein the bonding the integrated circuit chip to the bonding mask comprises flip-chip-bonding the integrated circuit chip to the bonding mask.

3. The method of claim 2, wherein the bonding the integrated circuit chip to the bonding mask further comprises:
   placing bump balls on electrode terminals of the integrated circuit chip; and
   inserting the bump balls into the through-holes while the integrated circuit chip is aligned with the bonding mask.

4. The method of claim 1, wherein the conductive material comprises conductive epoxy.

* * * * *